United States Patent
Cho et al.

(10) Patent No.: US 9,873,662 B2
(45) Date of Patent: *Jan. 23, 2018

(54) METAL PRECURSOR AND METAL PRECURSOR INK USING THE SAME

(71) Applicant: PESOLVE CO., LTD., Gyeonggi-do (KR)

(72) Inventors: Hyun Nam Cho, Gyeonggi-do (KR); Hyun Ju Kim, Gyeonggi-do (KR)

(73) Assignee: PESOLVE CO., LTD., Ansan-si, Gyeonggi-do (KR)

( * ) Notice: Subject to any disclaimer, the term of this patent is extended or adjusted under 35 U.S.C. 154(b) by 226 days.

This patent is subject to a terminal disclaimer.

(21) Appl. No.: 14/652,453

(22) PCT Filed: Dec. 9, 2013

(86) PCT No.: PCT/KR2013/011329
§ 371 (c)(1),
(2) Date: Jun. 16, 2015

(87) PCT Pub. No.: WO2014/098396
PCT Pub. Date: Jun. 26, 2014

(65) Prior Publication Data
US 2015/0336878 A1 Nov. 26, 2015

(30) Foreign Application Priority Data
Dec. 20, 2012 (KR) .................. 10-2012-0149495

(51) Int. Cl.
*C09D 11/52* (2014.01)
*C09D 11/30* (2014.01)
(Continued)

(52) U.S. Cl.
CPC ............ *C07C 251/38* (2013.01); *B05D 1/005* (2013.01); *B05D 3/007* (2013.01); *C07F 1/08* (2013.01);
(Continued)

(58) Field of Classification Search
CPC ....... C09D 11/52; C09D 11/30; C07C 251/38; C07F 1/08; C07F 1/10; C07F 15/06; C23C 18/08; B05D 1/005; B05D 3/007
(Continued)

(56) References Cited

U.S. PATENT DOCUMENTS 6,878,184 B1 4/2005 Rockenberger et al.
7,683,195 B2* 3/2010 Suganuma ............ C07C 51/00
427/255.28

(Continued)

FOREIGN PATENT DOCUMENTS

KR   10-2008-0013787 A   2/2008
KR   10-2012-0096499 A   8/2012
(Continued)

OTHER PUBLICATIONS

English translation of the Written Opinion of the International Search Authority dated Mar. 28, 2014 for PCT/KR2013/011329; 4 pages.*

(Continued)

*Primary Examiner* — Helene Klemanski
(74) *Attorney, Agent, or Firm* — STIP Law Group, LLC

(57) ABSTRACT

Provided are a metal precursor containing an oxime group, which is represented by general formula 1, and a metal precursor ink containing same. The metal precursor ink according to the present invention enhance metal content, induce intramolecular and/or intermolecular complexation, thereby enabling low temperature sintering with excellent solubility and stability. The metal precursor ink according to (Continued)

the present invention can be used to form a metal wire with a desired shape. Therefore, the metal precursor ink can find applications in the field of printed electronics, particularly various electrodes, such as mesh type transparent electrodes.

18 Claims, 8 Drawing Sheets

(51) Int. Cl.
| | | |
|---|---|---|
| C23C 18/08 | (2006.01) | |
| C07C 251/38 | (2006.01) | |
| C07F 1/08 | (2006.01) | |
| C07F 1/10 | (2006.01) | |
| C07F 15/06 | (2006.01) | |
| B05D 1/00 | (2006.01) | |
| B05D 3/00 | (2006.01) | |

(52) U.S. Cl.
CPC ............... *C07F 1/10* (2013.01); *C07F 15/06* (2013.01); *C09D 11/30* (2013.01); *C09D 11/52* (2013.01); *C23C 18/08* (2013.01)

(58) Field of Classification Search
USPC ....... 106/31.92; 252/519.2, 519.21; 564/256, 564/268
See application file for complete search history.

(56) References Cited

U.S. PATENT DOCUMENTS

| | | | |
|---|---|---|---|
| 7,691,294 B2 | 4/2010 | Chung et al. | |
| 8,070,986 B2 | 12/2011 | Heo et al. | |
| 8,226,755 B2 | 7/2012 | Chung et al. | |
| 9,683,123 B2* | 6/2017 | Cho ...................... | C09D 11/52 |
| 2008/0003364 A1 | 1/2008 | Ginley et al. | |
| 2010/0009153 A1 | 1/2010 | Yang et al. | |
| 2010/0022078 A1* | 1/2010 | Rockenberger ........ | C09D 11/52 438/585 |
| 2010/0084599 A1 | 4/2010 | Lewis et al. | |
| 2010/0181564 A1* | 7/2010 | Kuegler .............. | C23C 18/1216 257/43 |
| 2010/0189901 A1 | 7/2010 | Chung et al. | |
| 2010/0193751 A1* | 8/2010 | Heo .......................... | H01B 1/22 252/514 |
| 2011/0008548 A1 | 1/2011 | Smith et al. | |
| 2011/0111138 A1 | 5/2011 | McCullough et al. | |
| 2011/0183128 A1 | 7/2011 | Magdassi et al. | |
| 2011/0272691 A1* | 11/2011 | Kuegler ............... | C07C 249/08 257/43 |
| 2013/0102108 A1* | 4/2013 | Deshmukh .......... | C23C 18/1204 252/519.2 |
| 2014/0367676 A1* | 12/2014 | Haeming ............ | H01L 21/0237 257/43 |
| 2016/0168408 A1* | 6/2016 | Cho ...................... | C09D 11/52 252/519.3 |
| 2016/0185990 A1* | 6/2016 | Cho ...................... | C09D 11/52 252/519.21 |

FOREIGN PATENT DOCUMENTS

| | | |
|---|---|---|
| WO | 2007/004437 A1 | 1/2007 |
| WO | 2009/059273 A2 | 5/2009 |
| WO | WO2010011974 A1 | 1/2010 |
| WO | WO 2012/000594 A1 * | 1/2012 |

OTHER PUBLICATIONS

International Search Report for PCT/KR2013/011329 dated Mar. 28, 2014 from Korean Intellectual Property Office.
Lee et al., A Novel Solution-Stamping Process for Preparation of a Highly Conductive Aluminum Thin Film, Adv. Mater. 2011, 23, 5524-5528.
Binnemans et al., Structure and Mesomorphism of Silver Alkanoates, Chem. Mater. 2004, 16, 2021-2027.
Chun et al., Roll-to-Roll Printing of Silver Oxide Pastes and Low Temperature Conversion to Silver Patterns, Chem. 2009, 21, 343-350.
Sztyk et al., CVD of AgI Complexes with Tertiary Phosphines and Perfluorinated Carboxylates Ð A New Class of Silver Precursors, Chem. Vap. Deposition 2001, 7, No. 3.
Whitcomb et al., The molecular structure of [bis-triphenylphosphine-silver(I) stearate], [((C6 H5 )3 P)2 Ag(O2 C(CH2 ) 16 CH3 )], solubilization of long alkyl chain silver carboxylates, Chemical Crystallography. vol. 26, No. 2, 1996.
Wu et al., Synthesis of high-concentration Cu nanoparticles in aqueous CTAB solutions, Journal of Colloid and Interface Science 273 (2004) 165-169.
Balantrapu et al.,Silver nanoparticles for printable electronics and biological applications, J. Mater. Res., vol. 24, No. 9, Sep. 2009.
Smith et al., Direct ink-jet printing and low temperature conversion of conductive silver patterns, J Mater Sci 41 (2006) 4153-4158.
Grouchko et al., Formation of air-stable copper-silver core-shell nanoparticles for inkjet printing, J. Mater. Chem., 19, 3057-3062.
Walker et al., Reactive Silver Inks for Patterning High-Conductivity Features at Mild Temperatures, J. Am. Chem.Soc. 2012, 134, 1419-1421.
Dearden et al., A Low Curing Temperature Silver Ink for Use in Ink-Jet Printing and Subsequent Production of Conductive Tracks, Macromol. Rapid Commun. 2005, 26, 315-318.
Lee et al., Direct synthesis and inkjetting of silver nanocrystals toward printed electronics, Nanotechnology 17 (2006) 2424-2428.
Chi et al., Synthesis and Characterization of (β-Diketonato)silver Vinyltriethylsilane Compounds and Their Application to CVD of Silver Thin Films. Crystal Structure of the (2,2-Dimethyl-6,6,7,7,8,8,8-heptafluoro-3,5-octanedionato)silver Vinyltriethylsilane Dimer, Organometallics 1996, 15, 2575-2578.
Rozenberg et al., Synthesis and Spectroscopic Studies of Novel β-Diketonate Copper(I) Compounds and Solid State Structure of Tetravinylsilane Tetrakis Copper(I) 1,1,1,5,5,5-Hexafluoroacetylacetonate (TVST[Cu]hfac), Organometallics 2001, 20, 4001-4005.

* cited by examiner

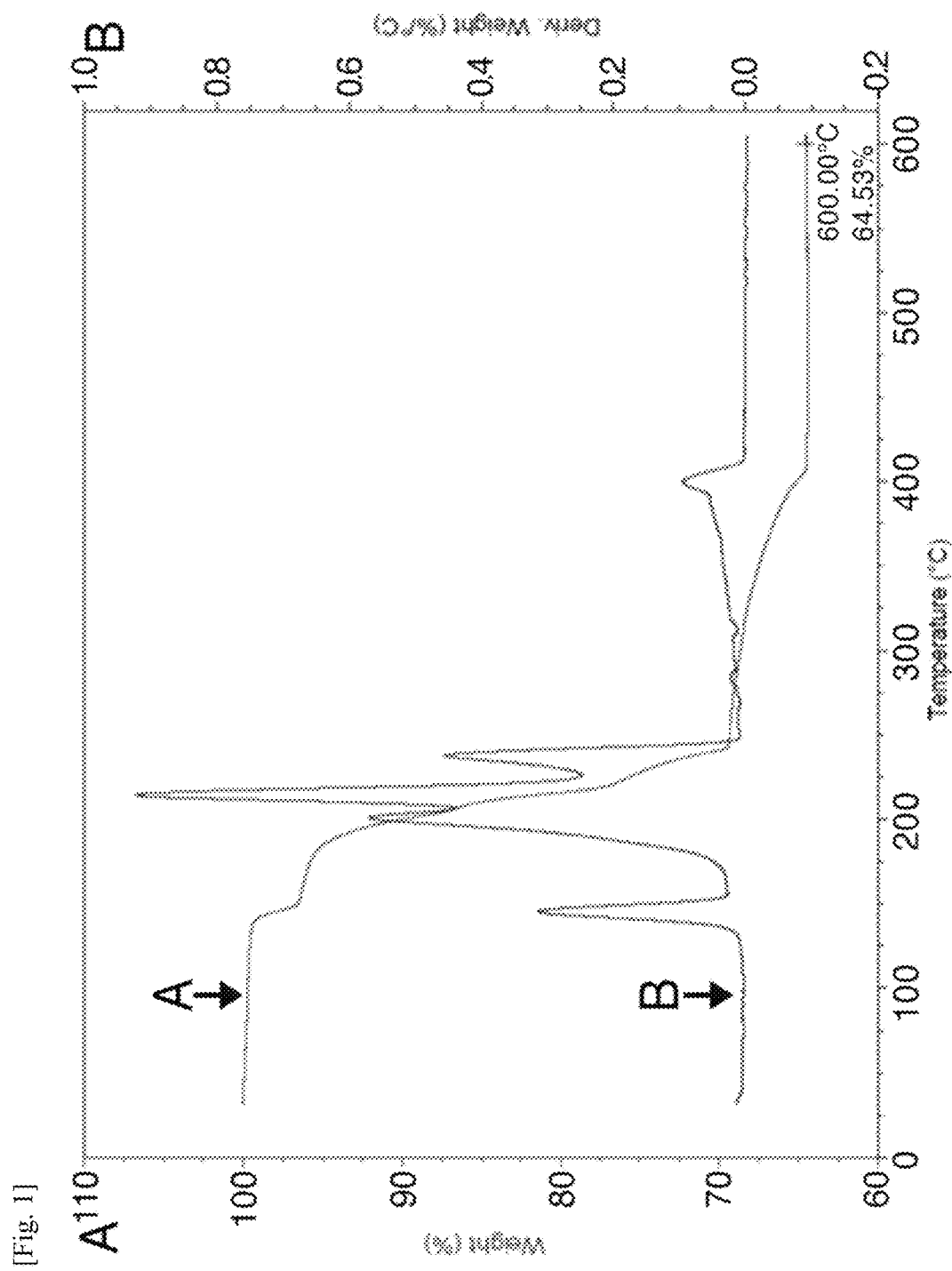
[Fig. 1]

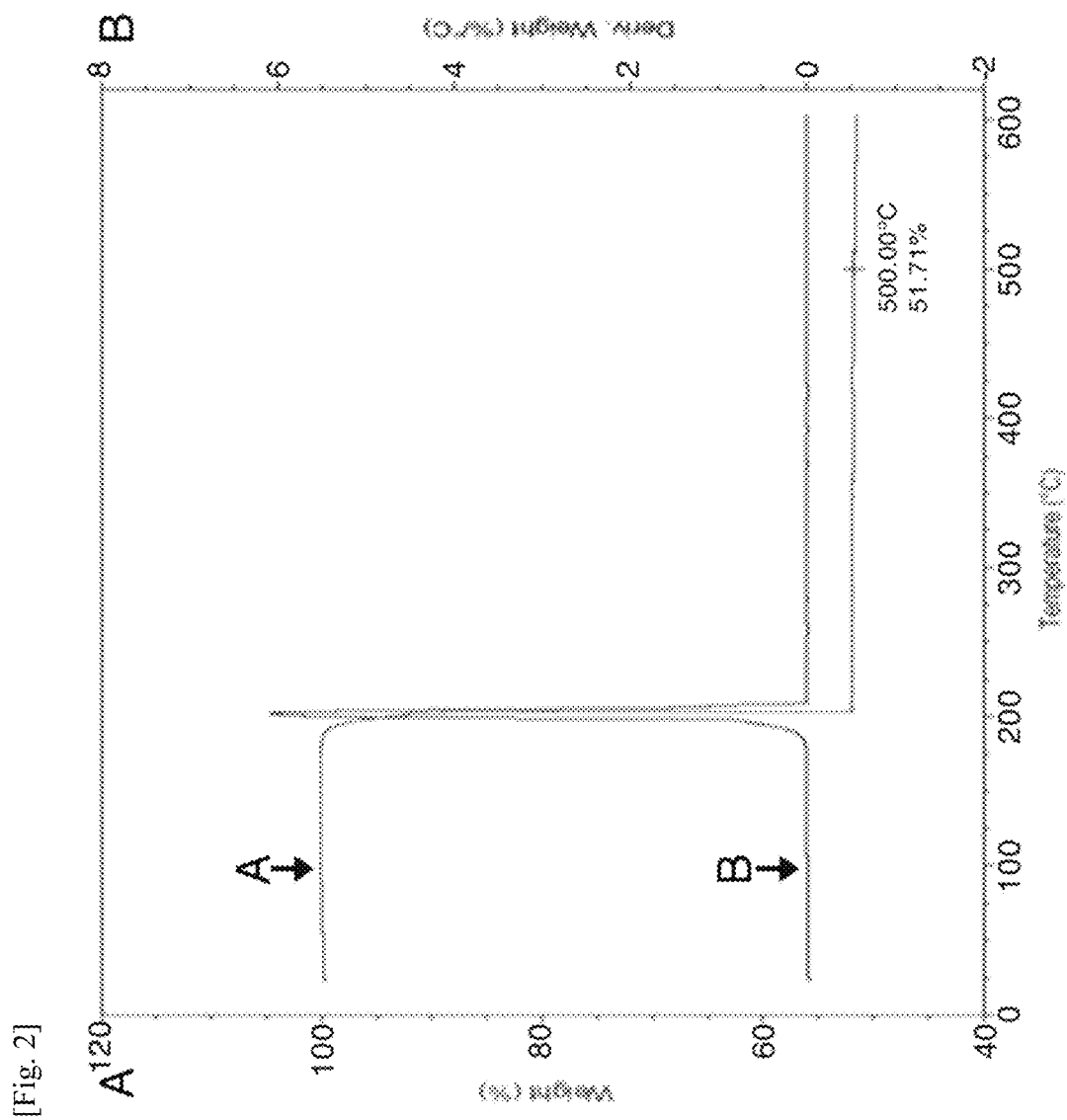
[Fig. 2]

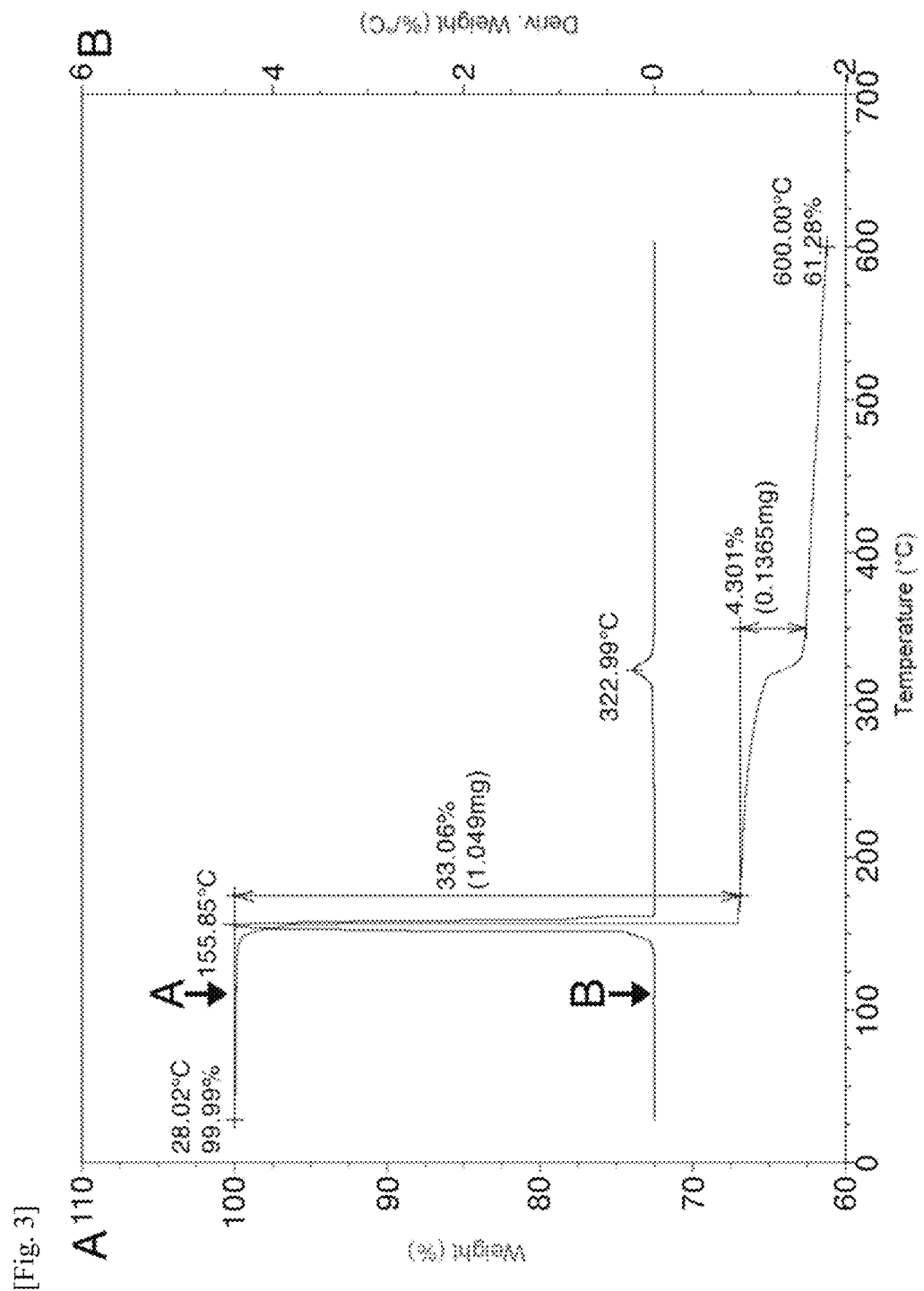
[Fig. 3]

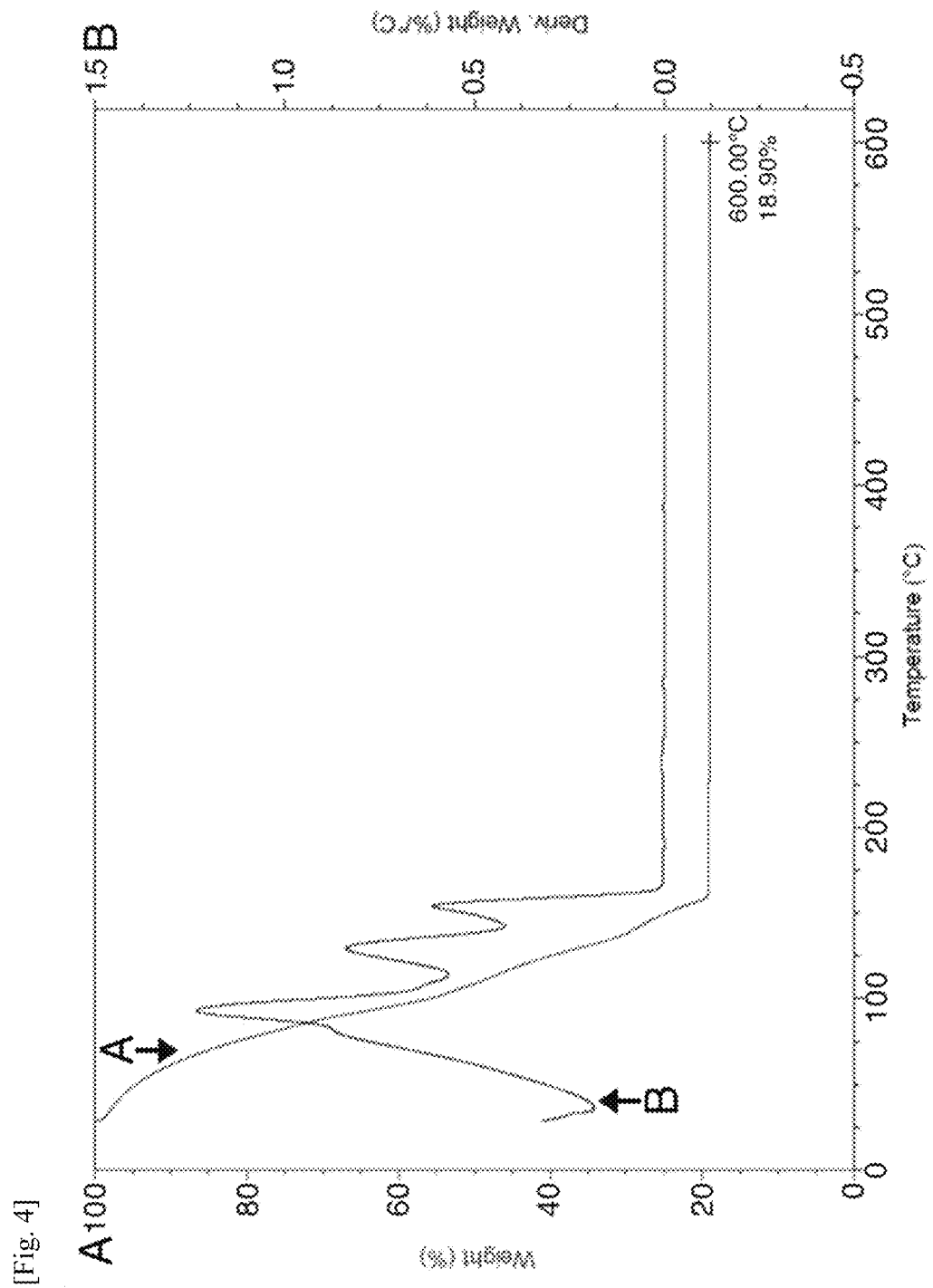
[Fig. 4]

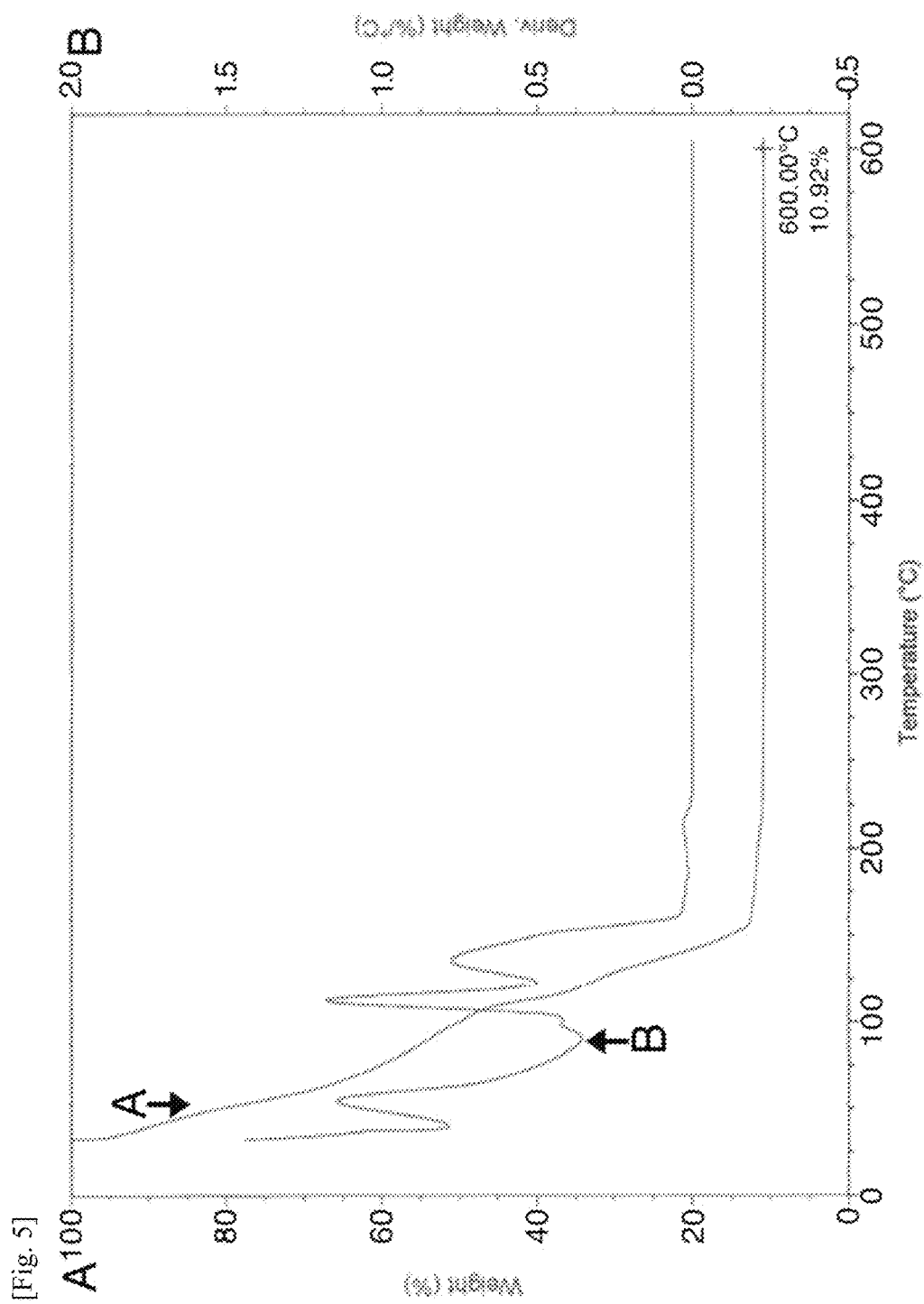
[Fig. 5]

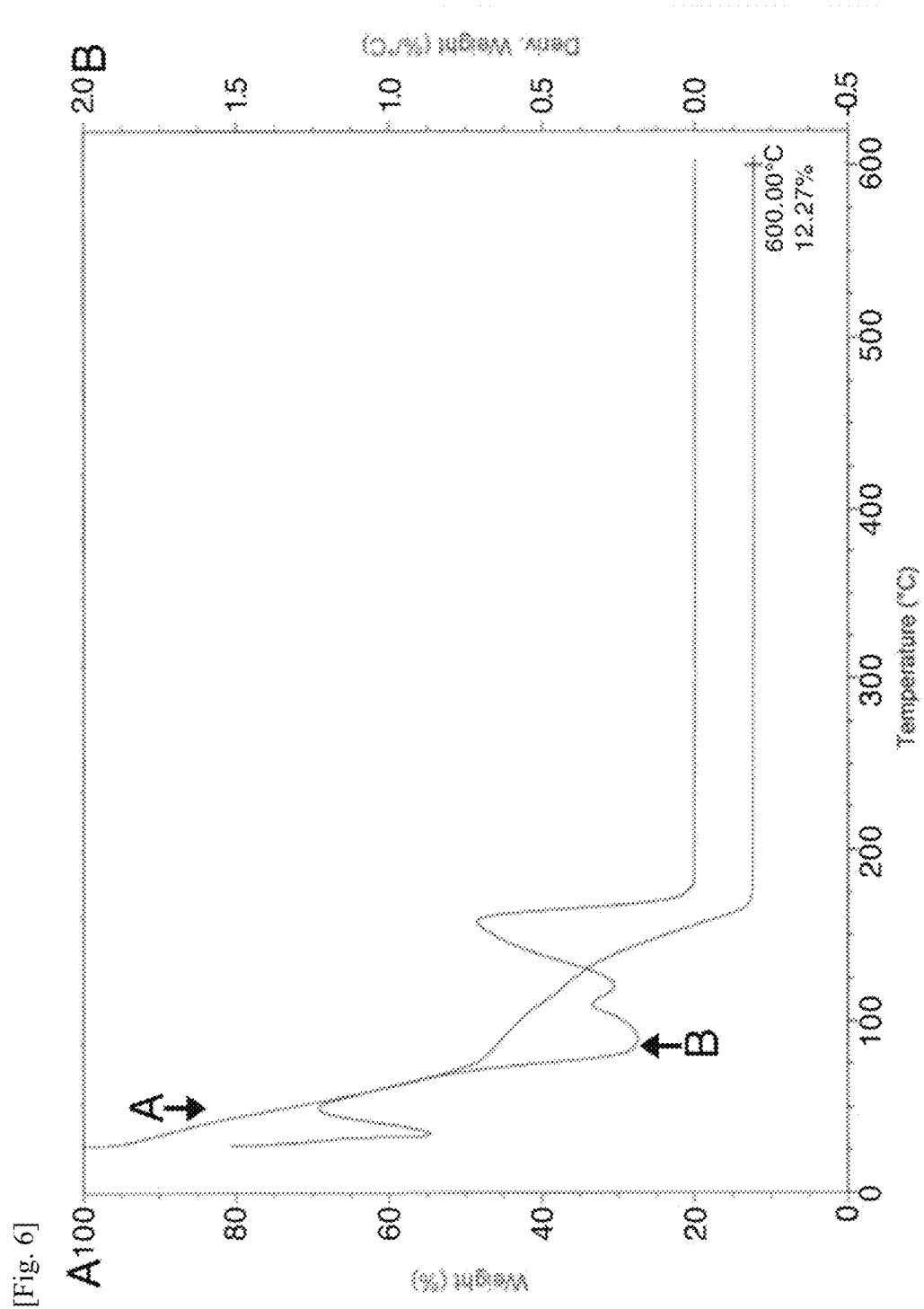
[Fig. 6]

[Fig. 7]
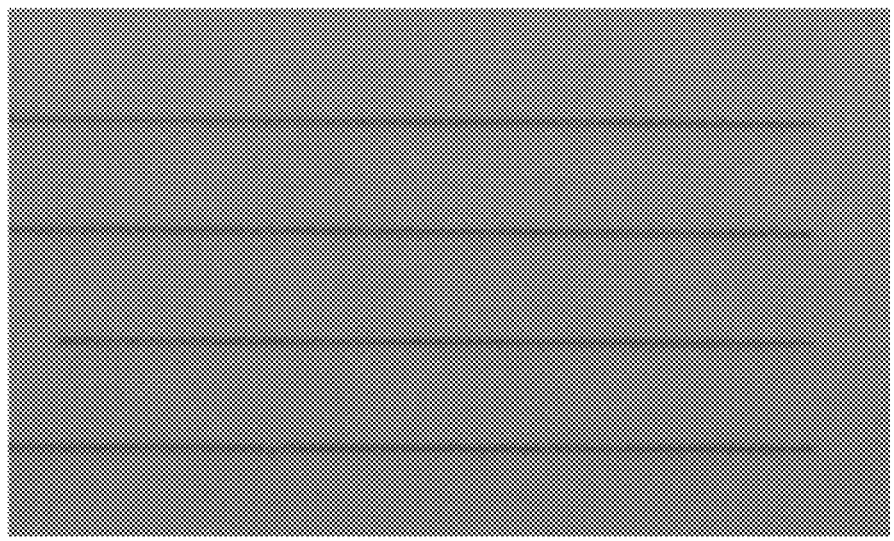
[Fig. 8]
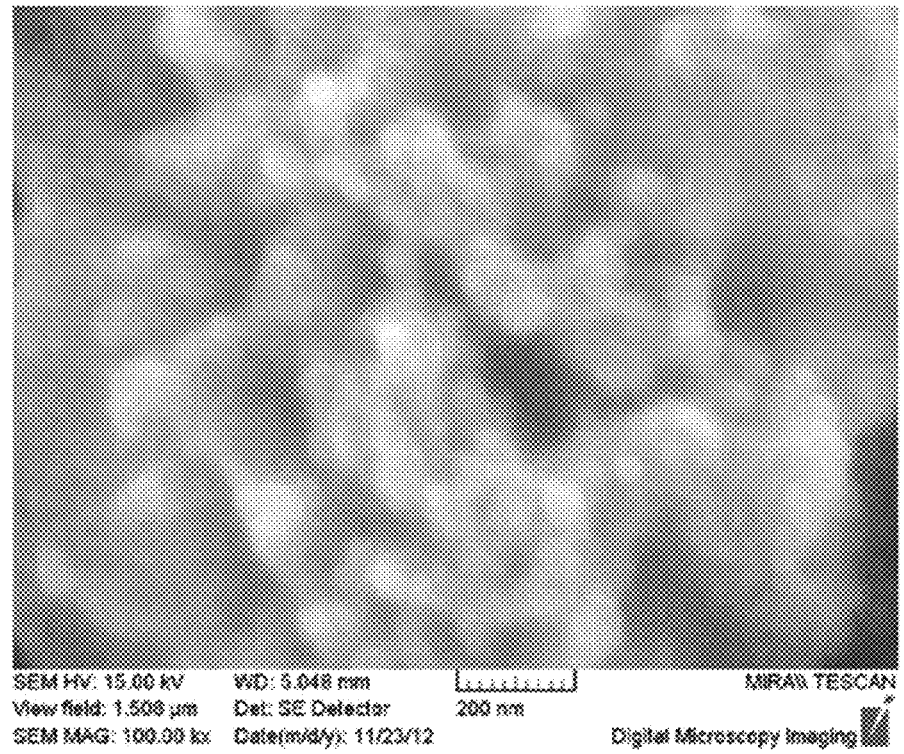

[Fig. 9]
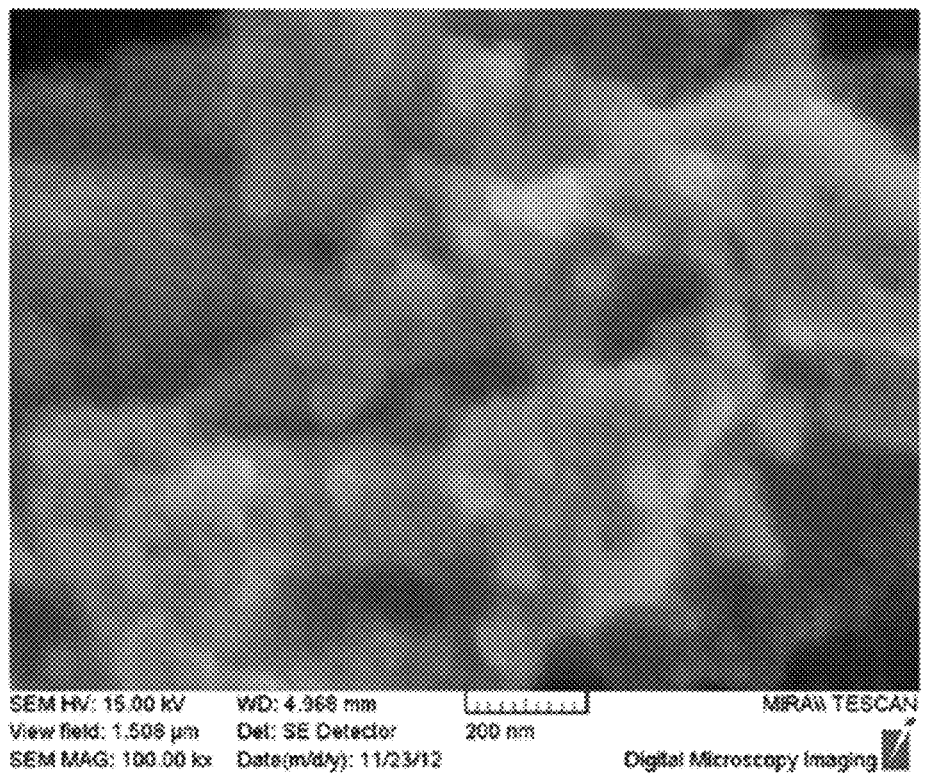

METAL PRECURSOR AND METAL PRECURSOR INK USING THE SAME

CROSS REFERENCE TO PRIOR APPLICATIONS

This application is a National Stage Application of PCT International Patent Application No. PCT/KR2013/011329 filed on Dec. 9, 2013, under 35 U.S.C. §371, which claims priority to Korean Patent Application No. 10-2012-0149495 filed on Dec. 20, 2012, which are all hereby incorporated by reference in their entirety.

TECHNICAL FIELD

The present invention relates to a metal precursor and a metal precursor ink using the same. More specifically, the present invention relates to a metal precursor and a metal precursor ink that don't have any particle form, enhance metal content, enable to low temperature calcination with excellent stability, and thus can find directly applications in the field of printed electronics.

BACKGROUND ART

In 21st century, the printed electronics industry has developed as environmental-friendly as well as convergence industry based on nanotechnology, and has been considered a new paradigm to overcome the limitations of existing industries. In the printed electronics industry, new concepts of electronic materials and components are produced based on printing processes for mass production at low temperature and ambient pressure, achieving low cost, flexibility, and large area of products.

Under such circumstances, it is anticipated that a new market for electronic products will be created in the future in response to emotions, consumption patterns, and diverse needs of consumers and its size will surpass that of the existing markets. Numerous printed electronic products have been developed, for example, RFIDs, memories, displays (for example, OLEDs, ELs, electronic papers, and flexible displays), lighting devices, batteries (for example, secondary batteries and solar cells), sensors, and organic transistors, printed circuit boards (for example, PCBs and FPCBs), touch panels, electrodes (including transparent electrodes), and applied products in the field of electromagnetic wave shielding. These printed electronic products have opened up new markets. With the emergence of price competitive and freely designable devices for printed electronic products, their market is expected to expand. Conventional processes for device production are partially limited by the kind and size of substrates employed, but printing processes are applicable irrespective of the kind, shape, and size of substrates. Particularly, printing processes are easily applied to large-size or flexible substrates and are recognized to be innovative in mass production of single products as well as small quantity batch production.

Suitable inks are essential for the manufacture of printed electronic products. Particularly, conductive inks are considered the most important materials. Specifically, an electronic ink composed of conductive metal nanoparticles or a metal precursor is directly printed (or coated) with an inkjet printer or a suitable printing system, such as a gravure printing, flexo printing, (rotary) screen printing, offset printing, gravure-offset printing or (nano)imprinting system, followed by drying or calcination to form a metal wire with a desired shape. This is essential for printed electronics processes.

Conductive inks necessary for printed electronics processes have been investigated and developed by many researchers. Generally, nanoparticle-based inks suffer from poor long-term storage stability or undergo aggregation of particles or precipitation, causing nozzle clogging during printing. For the purpose of preventing such problems, polymeric materials are usually used as stabilizers. However, excessive use of the stabilizers increases the viscosity of the inks or causes other problems, such as increased surface tension, high sintering temperature, and increased conductivity.

Conductive inks using metal nanoparticles can be found in Nanotechnology, 17, p2424 (2006), J. Mater. Res., 24, p 2828 (2009), J. Colloid Interface. Sci., 273, p165 (2004), J. Mater. Chem., 19, p 3057 (2009), US 2010/0084599 A1, US 2010/0009153A1, and US 2011/0183128A1.

The most commonly used approach to solve the problems of metal inks in the form of nanoparticles is to use organometallic salts or complexes as metal precursors. However, silver-containing carboxylic acid salts are generally sensitive to light, are not readily soluble, and have a high decomposition temperature, which limit their applicability despite ease of production. Attempts to solve such problems have been made, for example, by the use of silver precursors in which an electron donor, such as an amine or phosphine compound, is coordinated to a fluorinated carboxylic acid or a silver carboxylate having a long alkyl chain (Chem. Vapor Deposition, 7, pill (2001)), Organometallics, 15, p 2575 (1996), Chem. Mater., 16, p 2021 (2004), and J. Chem. Crystallography, 26, p 99 (1996), inks using an organometallic complex or metal salt (U.S. Pat. No. 7,691,294 B2, US 2011/0111138A1, U.S. Pat. No. 8,226,755 B2, and J. Am. Chem. Soc., 134, 1419, 2012), an ink containing silver β-ketocarboxylate (WO 2007/004437A1), and inks using a silver neoalkanoate (Makromol Rapid Commun., 26, p 315 (2005), J. Mater. Sci., 41, p 4153 (2006), Chem. Mater., 21, p 343 (2009) and US 2011/0008548A1)). Inexpensive copper and aluminum precursor inks as well as silver precursor inks have alos been developed (Organometallics, 20, p 4001 (2001), US 2008/0003364A1, Adv. Mater., 23, 5524, 2011, WO 2009/059273A2, and WO 2010/011974A1).

However, such metal complex inks have low metal solid contents or suffer from poor storage stability, which limit their application to products where highly reliable and conductive metal wires are needed.

DETAILED DESCRIPTION OF THE INVENTION

Problems to be Solved by the Invention

An object of the present invention is to provide a metal precursor ink that enhance metal content, and enable low temperature sintering with excellent solubility and stability.

Means for Solving the Problems

According to one aspect of the present invention, there is provided novel metal precursor having an oxime group, represented by the following General Formula 1:

[General Formula 1]

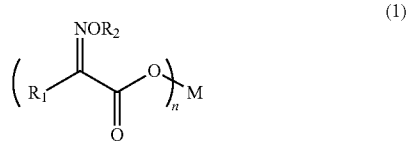

(1)

wherein $R_1$ and $R_2$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, —$(CH_2)_jOR^a$, —$(CH_2)_jC(O)Ra$, —$(CH_2)_jC(O)OR^a$, —$(CH_2)_jOC(O)R^a$, —$(CH_2)_jOM$, —$(CH_2)_jC(O)M$, —$(CH_2)_jC(O)OM$, —$(CH_2)_jOC(O)M$, —$(CH_2)_jNR^bR^c$, —$(CH_2)_jC(O)NR^bR^c$, —$(CH_2)_jOC(O)NR^bR^c$, —$(CH_2)_jNR^dC(O)R^b$, —$(CH_2)_jNR^dC(O)OR^b$, —$(CH_2)_jNR^dC(O)NR^bR^c$, —$(CH_2)_jS(O)_mR^e$ or —$(CH_2)_jNR^dS(O)_mM$, where j is an integer from 0 to 12, m is an integer from 0 to 2, and $R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl, n is an integer from 1 to 4, and M is a monovalent- to tetravalent metal.

According to a further aspect of the present invention, there is provided the metal precursor ink comprising one or more kinds of the metal precursor and one or more additives selected from the group consisting of a solvent, a complexing agent, a resin, a stabilizer, a dispersant, a reducing agent, a coupling agent, a leveling agent, a surfactant, a wetting agent, a thickening agent, and a thixotropic agent.

According to another aspect of the present invention, there is provided a conductive thin film formed by deposition of the metal precursor ink.

Effects of the Invention

The metal precursor ink according to the present invention enhance metal content, and induce intramolecular and/or intermolecular complexation, thereby enabling low temperature sintering with excellent solubility and stability.

BRIEF DESCRIPTION OF THE DRAWINGS

FIG. 1 shows TGA pyrolysis curves of a silver precursor compound prepared in Example 1.
FIG. 2 shows TGA pyrolysis curves of a silver precursor compound prepared in Example 11.
FIG. 3 shows TGA pyrolysis curves of a silver precursor compound prepared in Example 13.
FIG. 4 shows TGA pyrolysis curves of a silver precursor ink produced in Example 16.
FIG. 5 shows TGA pyrolysis curves of a silver precursor ink produced in Example 20.
FIG. 6 shows TGA pyrolysis curves of a silver precursor ink produced in Example 23.
FIG. 7 is an image of a silver precursor ink produced in Example 16 and printed on a PET film with an inkjet printer.
FIG. 8 is a surface electron microscopy (SEM) image of a silver precursor ink produced in Example 16 and printed with an inkjet printer.
FIG. 9 is a surface electron microscopy (SEM) image of a silver precursor ink produced in Example 20 and printed with an inkjet printer.

MODE FOR CARRYING OUT THE INVENTION

The term "alkyl" used herein includes straight-chain, branched-chain, or cyclic hydrocarbon radicals, and combinations thereof, and may optionally include one or more double bonds, triple bonds or a combination thereof in the chain. That is, "alkyl" is intended to include alkenes or alkynes.

The term "heteroalkyl", by itself or in combination with another term, unless otherwise stated, means a stable straight-chain, branched-chain, or cyclic hydrocarbon radical or a combination thereof, consisting of one or more carbon atoms and one or more heteroatoms selected from the group consisting of O, N, P, Si, and S, and wherein the nitrogen, phosphorus, and sulfur atoms may optionally be oxidized and the nitrogen heteroatom may optionally be quaternized.

The terms "cycloalkyl" and "heterocycloalkyl", by themselves or in combination with other terms, unless otherwise stated, represent cyclic versions of "alkyl" and "heteroalkyl", respectively.

The term "aryl" means, unless otherwise stated, a polyunsaturated, aromatic, hydrocarbon substituent which can be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. The heteroaryl group can be attached to the remainder of the molecule through a carbon or heteroatom.

The term "aralkyl" refers to an alkyl group substituted with an aryl group wherein the alkyl and aryl moieties independently are optionally substituted.

The term "heteroaralkyl" refers to an alkyl group substituted with an aryl group and a heteroaryl group wherein the alkyl and heteroaryl moieties independently are optionally substituted.

The term "substituted" in the expression of "substituted or unsubstituted" described herein means that one or more hydrogen atoms in the hydrocarbon are each independently replaced by the same or different substituents.

Suitable substituents include, but are not limited to, —F; —Cl; —Br; —CN; —NO$_2$; —OH; $C_1$-$C_{20}$ alkyl groups substituted or unsubstituted with —F, —Cl, —Br, —CN, —NO$_2$ or —OH; $C_1$-$C_{20}$ alkoxy groups substituted or unsubstituted with —F, —Cl, —Br, —CN, —NO$_2$ or —OH; $C_6$-$C_{30}$ aryls groups substituted or unsubstituted with $C_1$-$C_{20}$ alkyl, $C_1$-$C_{20}$ alkoxy, —F, —Cl, —Br, —CN, —NO$_2$ or —OH; $C_6$-$C_{30}$ heteroaryl groups substituted or unsubstituted with $C_1$-$C_{20}$ alkyl, $C_1$-$C_{20}$ alkoxy, —F, —Cl, —Br, —CN, —NO$_2$ or —OH; $C_5$-$C_{20}$ cycloalkyl groups substituted or unsubstituted with $C_1$-$C_{20}$ alkyl, $C_1$-$C_{20}$ alkoxy, —F, —Cl, —Br, —CN, —NO$_2$ or —OH; $C_5$-$C_{30}$ heterocycloalkyl groups substituted or unsubstituted with $C_1$-$C_{20}$ alkyl, $C_1$-$C_{20}$ alkoxy, —F, —Cl, —Br, —CN, —NO$_2$ or —OH; and groups represented by —N(G$_1$)(G$_2$), where G$_1$ and G$_2$ may be each independently hydrogen; $C_1$-$C_{10}$ alkyl group; or $C_6$-$C_{30}$ aryl group substituted or unsubstituted with $C_1$-$C_{10}$ alkyl.

One embodiment of the present invention provides the metal precursor ink enabling low temperature calcination with excellent solubility and stability by adding an oxime group and/or an oxime derivative thereof into the metal precursor compound.

Specifically, the metal precursor ink according to the above embodiment of the present invention includes as a major component, the compound having the oxime group or the oxime derivative thereof, represented by the following General Formula 1:

[General Formula 1]

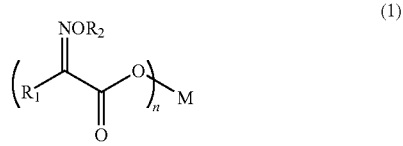

(1)

In the above General Formula 1, $R_1$ and $R_2$ are each independently hydrogen, a $C_1$-$C_{30}$ aliphatic or $C_1$-$C_{30}$ alicyclic alkyl group, an aryl group, an aryl-alkyl group, an acyl group, an alkyl or aryl group having substituted functional group, a hetero compound or its derivative, a halogen compound or its derivative, or a metal or a metal compound, but are not particularly limited thereto.

Preferably, $R_1$ and $R_2$ are defined below.

In the above General Formula 1, $R_1$ and $R_2$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, $-(CH_2)_jOR^a$, $-(CH_2)_j C(O)R^a$, $-(CH_2)_j C(O)OR^a$, $-(CH_2)_jOC(O)R^a$, $-(CH_2)_jOM$, $-(CH_2)_jC(O)M$, $-(CH_2)_jC(O)OM$, $-(CH_2)_jOC(O)M$, $-(CH_2)_jNR^bR^c$, $-(CH_2)_jC(O)NR^bR^c$, $-(CH_2)_jOC(O)NR^bR^c$, $-(CH_2)_jNR^dC(O)R^b$, $-(CH_2)_jNR^dC(O)OR^b$, $-(CH_2)_jNR^dC(O)NR^bR^c$, $-(CH_2)_jS(O)_mR^e$ or $-(CH_2)_jNR^dS(O)_mM$, where j is an integer from 0 to 12, m is an integer from 0 to 2.

$R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl.

In Formula 1, n is an integer from 1 to 4 and M is a monovalent to tetravalent metal. The metal may be, for example, selected from the group consisting of Ag, Cu, Ni, Co, Zn, Mn, Sn, Au, Pt, Pd, Sb, Bi, Pb, Ti, Zr, and Hf, but is not particularly limited thereto.

More specifically, $R_1$ and $R_2$ may be each independently selected from the group consisting of hydrogen, methyl, ethyl, n-propyl, iso-propyl, n-butyl, iso-butyl, t-butyl, n-pentyl, amyl, n-hexyl, 2-ethylhexyl, n-heptyl, octyl, iso-octyl, nonyl, decyl, dodecyl, hexadecyl, octadecyl, docodecyl, cyclopropyl, cyclopentyl, cyclohexyl, allyl, propargyl, acetyl, benzoyl, hydroxyethyl, methoxyethyl, 2-hydroxypropyl, methoxypropyl, aminoethyl, cyanoethyl, mercaptoethyl, chloroethyl, methoxy, ethoxy, butoxy, hexyloxy, phenoxy, methoxyethoxyethyl, methoxyethoxyethoxyethyl, imidazole, carboxymethyl, trimethoxysilylpropyl, triethoxysilylpropyl, phenyl, methoxyphenyl, cyanophenyl, tolyl, benzyl, derivatives thereof, and carboxylic acid metal salts, but are not particularly limited thereto.

Preferably, the compound of the above General Formula 1 is selected from the group consisting of compounds represented by the following General Formulae 2 to 5:

[General Formula 2]

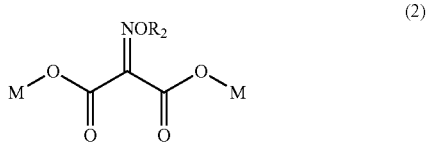

(2)

[General Formula 3]

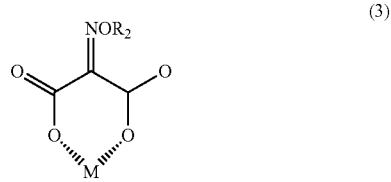

(3)

[General Formula 4]

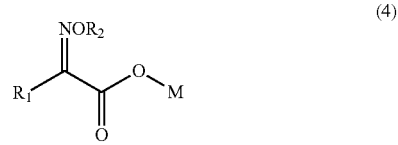

(4)

[General Formula 5]

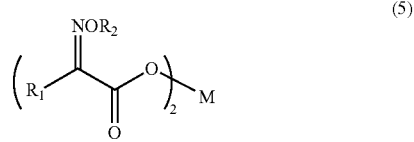

(5)

More specific examples of such metal precursor compounds may be represented as the following Formulae 1 to 15:

[Formula 1]

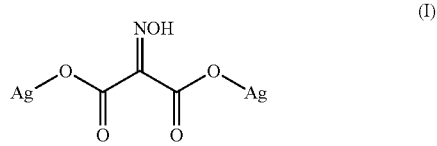

(I)

[Formula 2]

$$\text{Ag-O-C(=O)-C(=NOCH}_3\text{)-C(=O)-O-Ag}$$ (II)

[Formula 3]

(III) Ag-O-C(=O)-C(=N-O-CH$_2$-CH(C$_2$H$_5$)-C$_4$H$_9$)-C(=O)-O-Ag

[Formula 4]

(IV) Ag-O-C(=O)-C(=N-O-CH$_2$-CH=CH$_2$)-C(=O)-O-Ag

[Formula 5]

(V) Ag-O-C(=O)-C(=N-O-CH$_2$-C≡CH)-C(=O)-O-Ag

[Formula 6]

(VI) Cu complex of 2-(hydroxyimino)malonate

[Formula 7]

(VII) Cu complex of 2-(2-ethylhexyloxyimino)malonate

[Formula 8]

(VIII) Ni complex of 2-(2-ethylhexyloxyimino)malonate

[Formula 9]

(IX) Co complex of 2-(2-ethylhexyloxyimino)malonate

[Formula 10]

(X) Ag salt of (hydroxyimino)acetate

[Formula 11]

(XI) Ag salt of 2-(hydroxyimino)propanoate

[Formula 12]

(XII) Ag salt of 2-(methoxyimino)propanoate

[Formula 13]

(XIII) Cu bis[(hydroxyimino)acetate]

[Formula 14]

(XIV) Cu bis[2-(hydroxyimino)propanoate]

[Formula 15]

(XV) Ni bis[2-(hydroxyimino)propanoate]

There is no particular restriction on the structure and preparation method of the above Formulae. For example, the metal precursor may be prepared by the following procedure. First, starting materials for the metal precursor are prepared by methods described in the literature or suitable modifications thereof. The materials may be directly prepared and used when they are not known or their preparation methods are not described in the literature. The oxime or derivative thereof may be prepared by general methods well known in the literature, for example, a method for preparing a ketoxime or aldoxime by reacting a hydroxylamine derivative, such as a hydroxylamine or alkoxyamine, with a ketone or aldehyde compound. Alternatively, the oxime or derivative thereof having an electron withdrawing group may be prepared using sodium nitrite. Representative methods are depicted in the following schemes 1 to 4:

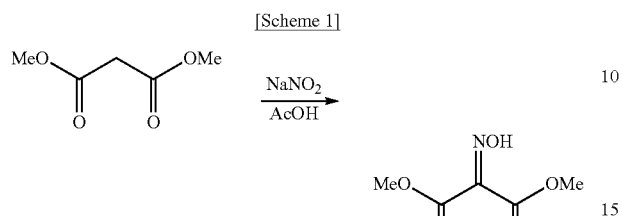

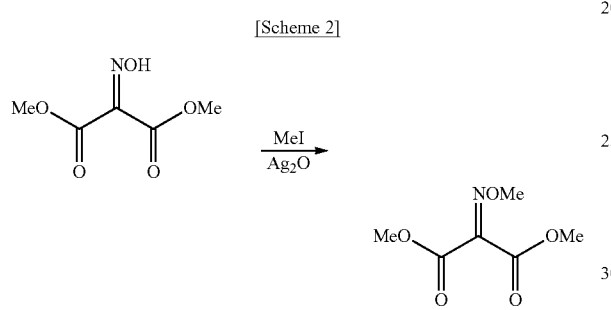

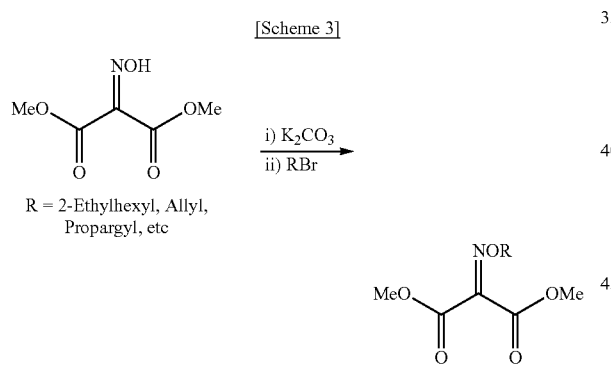

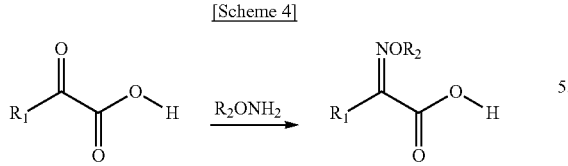

The metal precursor may be prepared by different methods depending on the kind of the metal and the metal salt. However, any method that does not impair the object of the present invention may be used to prepare the metal precursor. Exemplary methods for preparing the metal precursor are depicted in the following schemes 5 to 8.

The metal precursor is usually prepared by hydrolysis of a methyl (or ethyl) ester compound in an aqueous solution of sodium hydroxide at room temperature or under reflux in an ethanolic solution of potassium hydroxide, followed by reaction with silver nitrate. When there is a difficulty in performing hydrolysis, an acid is prepared and then reacted with caustic soda to form corresponding sodium salt, and followed by reaction with silver nitrate to substitute the sodium with silver. Particularly, the reaction mixture may be strongly basic upon reaction with silver nitrate. In this case, the reaction mixture is first neutralized with dilute nitric acid to prevent any oxidation of the silver nitrate and then the silver precursor is prepared. More detailed cases are exemplified in the Examples section that follows.

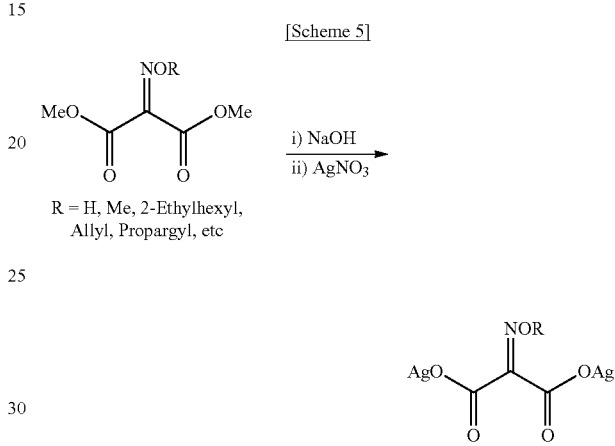

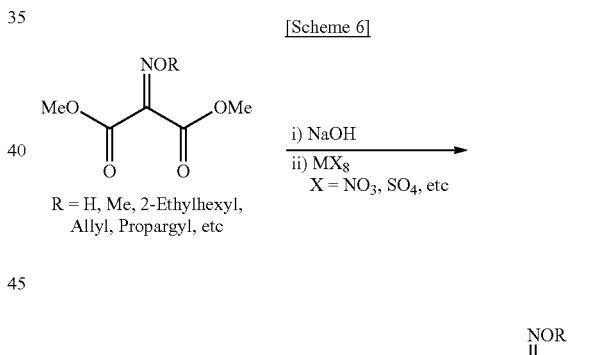

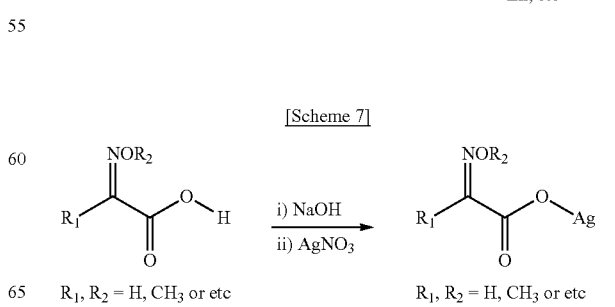

[Scheme 8]

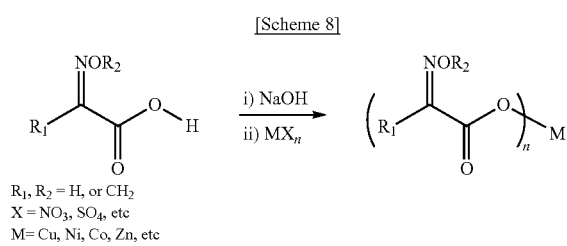

$R_1, R_2$ = H, or $CH_2$
X = $NO_3$, $SO_4$, etc
M = Cu, Ni, Co, Zn, etc

As can be seen from the foregoing structures and schemes, the metal precursor may have various structures and molecular weights so long as the object of the present invention is not impaired. The precursor is required to have a high metal content, high solubility, good stability, and form a high quality metal thin film. To meet these requirements, it is preferred that the precursor has as many metal atoms (particularly, silver atoms) as possible in one molecule, like a compound of the following General Formula 6.

The compound of the following General Formula 6 may be prepared as depicted in Scheme 9 or 10:

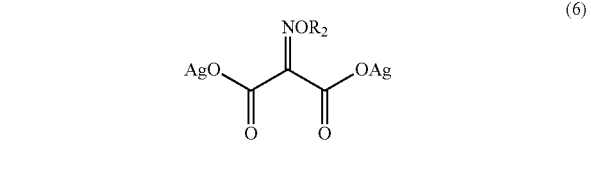

(6)

[Scheme 9]

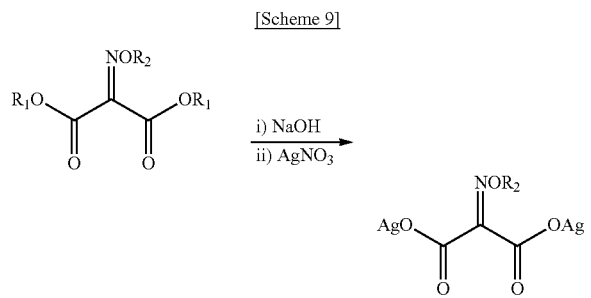

[Scheme 10]

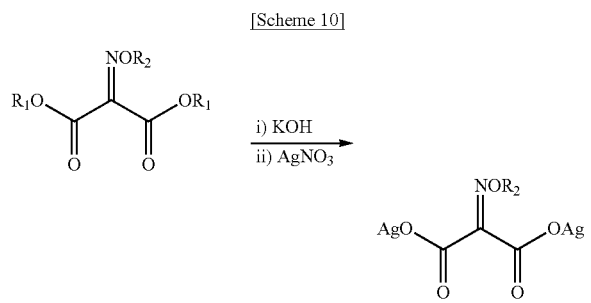

Methods for preparing the precursor compounds represented by the foregoing structures and shown in the foregoing schemes will be explained in more detail in the Examples section that follows.

Various solvents and compounds are required to produce inks from the metal precursors.

For example, a complexing agent or ligand is generally required to more easily dissolve a higher concentration of the metal precursor in a general solvent. Such complexing agents or ligands are well known and are mostly electron donors. Examples of the compounds include amine compounds having nitrogen atom, mercaptan compounds having sulfur atom, and phosphine compounds having phosporus atom, which are all sigma-electron donors and are known to be involved in complex formation. These compounds may be used in combination as a mixture thereof.

The amine compounds may be, for example, ammonia, primary amines, secondary amines, tertiary amines, and/or quaternary ammonium salts. The amines may be substituted with an alkyl, aryl or aralkyl group. Particularly, the alkyl may be linear, branched or cyclic in shape. The amines may also be multi-amines or amines having a functional group, such as a hydroxyl, alkoxy, ester, amide or urethane group. Specific examples of the amines include ammonia, methylamine, ethylamine, n-propylamine, isopropylamine, n-butylamine, isobutylamine, t-butylamine, isoamylamine, n-hexylamine, diethylamine, triethylamine, amylamine, 2-ethylhexylamine, cyclohexylamine, allylamine, propargylamine, ethylenediamine, monoethanolamine, diethanolamine, 1-amino-2-propanol, 3-amino-1-propanol, 2-amino-2-methyl-1-propanol, N,N-diethylhydroxylamine, methoxyethylamine, N,N-diethylethylenediamine, N,N,N'N'-tetramethylethylenediamine, pyridine, morpholine, imidazole, benzylamine, phenethylamine, ammonium carbamate, ammonium carbonate, tetraethylammonium bicarbonate, tetraethylammonium bromide, tetrabutylammonium hydroxide, polyethyleneimine, polyvinylamine, aminopropyltriethoxysilane, and derivatives thereof. The number of carbon atoms of the amines is preferably 20 or lower ($C_{20}$) but is not particularly limited thereto.

Examples of the phosphine compounds include trimethylphosphine, tributylphosphine, and triphenylphosphine. Representative examples of the sulfur compounds include ethanethiol, dodecylthiol, dimethyl sulfide, tetrahydrothiophene, bismuthiol, and mercaptopropyltrimethoxysilane.

Phi-electron donors are also involved in complex formation and are mostly compounds having a double or triple bond. Some phi-electron donors can strongly form complexes and some can weakly form complexes. Accordingly, suitable phi-electron donors can be selected according to the intended needs. Examples of the phi-electron donors include cyclooctadiene, butadiene, norbornadiene, allyl alcohol, vinyltriethylsilane, propargyl alcohol, 1-ethynylcyclohexanol, 3-butyne-2-ol, 2-methyl-3-butyne-2-ol, 3-methyl-1-pentyne-3-ol, and 3,5-dimethyl-1-hexyne-3-ol (Surfynol 61).

The amount of electron donor used is not necessarily limited but is typically in the range of 0.5 to 95% by weight, preferably 0.5 to 50% by weight, more preferably 0.5 to 25% by weight, based on the weight of the metal precursor.

In addition to the nitrogen atom of the imine group as a sigma-electron donor involved in complexation in the molecule, the metal precursor having an oxime group or a derivative thereof may have a double bond, such as an allyl group, or a triple bond, such as a propargyl group, capable of phi-complexation according to its structure. The presence of the multiple bond makes the metal precursor advantageous in producing a highly soluble precursor ink having a high concentration. Such materials are expected to be directly or indirectly involved in intramolecular and/or intermolecular complexation with other electron donors. For example, a metal (silver) precursor of Formula 16 may form an intramolecular complex, and Structure 17 shows a model of an intramolecular metal complex.

[Formula 16]

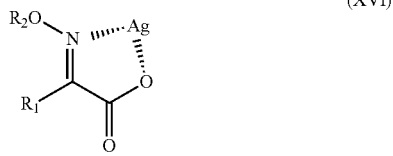

(XVI)

[Formula 17]

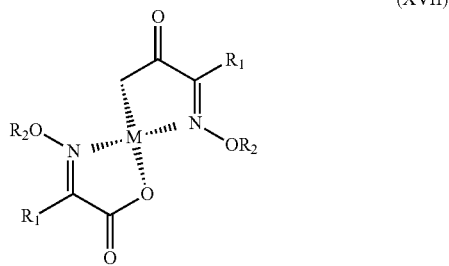

(XVII)

Such complexation weakens the metal-ester bond strength, which is expected to affect the solubility and calcination of the metal precursor. For example, 1 to 2 g of aqueous ammonia (28 to 30 wt %) is sufficient to dissolve 1 g of the compound (I) of Formula 1. The compound (III) of Formula 3 is soluble to some extent in dimethyl sulfoxide (DMSO) alone. Particularly, the compound (III) of Formula 3 is highly soluble in general amine compounds, such as isobutylamine, 2-ethylhexylamine, N,N-diethylethylenediamine, and N,N,N',N'-tetramethylethylenediamine. Even when a mixture of the amine compound and methanol or ethanol as a solvent is used, a transparent ink can be produced.

The metal precursor ink of the present invention may further include one or more additives selected from the group consisting of a solvent, a resin, a stabilizer, a dispersant, a reducing agent, a coupling agent, a leveling agent, a surfactant, a wetting agent, a thickening agent, and a thixotropic agent, which are required to control the viscosity of the ink or facilitate the formation of a thin film.

Specific examples of the solvent include water, methanol, ethanol, isopropanol, butanol, benzyl alcohol, diacetone alcohol, methoxyethanol, ethoxyethanol, butoxyethanol, ethylene glycol, diethylene glycol, propylene glycol monomethyl ether, monoglyme, diglyme, butyl carbitol, α-terpineol, glycerin, ethyl acetate, butyl acetate, ethyl lactate, carbitol acetate, acetone, methyl ethyl ketone, cyclohexanone, chloroform, methylene chloride, diethyl ether, tetrahydrofuran, dioxane, hexane, cyclohexane, heptane, dimethylformamide, dimethylacetamide, dimethyl sulfoxide, N-methylpyrrolidone, benzene, toluene, and xylene, and mixed solvents thereof. Examples of the resin include acrylic, polyvinyl, polyolefin, polyester, polyamide, polyurethane, polysulfone, epoxy, phenolic, phenoxy, alkyd, melamine, urea, silicone, fluorinated, and cellulose. Other examples of the resin are water-soluble resins, thermoplastic resins, heat curable resins, and UV curable resins, such as latex and natural resins. The stabilizer serves to stabilize the ink. Examples of the stabilizer include organic acids, such as formic acid and acetic acid, inorganic acids, such as sulfuric acid or phosphoric acid, fatty acids, such as neodecanoic acid or stearic acid, and acid derivatives, such as fatty acid metal salts. The reducing agent may be, for example, hydrazine, sodium borohydride, formaldehyde, ammonium formate or glucose. As the coupling agent, there may be used silane coupling agents, such as trimethoxypropylsilane and vinyltriethoxysilane, titanium-based coupling agents, zirconium-based coupling agents, and aluminum-based coupling agents. The surfactant is typically nonionic, anionic, cationic, and amphoteric surfactants. As the wetting agent, there may be used, for example, propylene glycol, butanediol, pentanediol, hexanediol, polyethylene glycol, and Surfynol series available from Air Products. As the thickener, there may be used, for example, hydroxypropyl cellulose and Bentone. As the leveling agent, there may be used, for example, BYK series. However, the amounts of these additives used are not particularly limited so long as the characteristics of the ink according to the present invention are not sacrificed.

The metal precursor ink of the present invention may include one or more the metal precursor represented by General Formula 1 and one or more additives selected from the group consisting of ammonia, ammonium formate, ammonium carbamate, isobutylamine, ethylhexylamine, diethanolamine, propylene glycol, 2,3-butanediol, methanol, and 2-amino-2-methyl-1-propanol, as described in the Examples section that follows.

The metal precursor ink of the present invention is not necessarily limited to a particular viscosity so long as a thin film and a pattern can be formed by suitable coating and printing techniques without causing any problem. The viscosity of the metal precursor ink is preferably from 0.1 to 1,000,000 cps, more preferably from 1 to 100,000 cps. For example, the viscosity of the ink is very important when a thin film and a pattern are formed by inkjet printing. The viscosity of the ink is typically in the range of 0.1 to 50 cps, preferably 1 to 20 cps, more preferably 3 to 15 cps, as measured at room temperature 20° C. If the viscosity of the ink is less than the lower limit defined above, the ink may spread or the thickness of a thin film after calcination is not sufficient, tending to deteriorate the conductivity of the thin film. Meanwhile, if the viscosity of the ink exceeds the upper limit defined above, the ink is not readily ejected through a nozzle.

So long as the object of the present invention is not impaired, the method for producing the metal precursor ink of the present invention is not particularly limited. For example, there is no particular restriction on the solvent, reaction temperature, concentration, pressure or whether a catalyst is used.

The metal precursor and the ink of the present invention can be used to produce hybrid inks Specifically, hybrid inks may be produced by mixing or reacting the metal precursor and the ink of the present invention with one or more materials selected from the group consisting of other known metal precursor compounds, metal powders, metal nanoparticles, and inks produced therefrom. Examples of such materials include silver acetate, silver trifluoroacetate, silver 1,3-acetonedicarboxylate, silver acetoacetate, silver oxalate, silver lactate, silver malonate, silver maleate, silver fumarate, silver glyoxylate, silver pyruvate, silver succinate, silver glutalate, silver picrate, silver citrate, silver nitrilotriacetate, silver ethylenediaminetetraacetate, silver neodecanoate, silver stearate, silver oxide, silver carbonate, microparticles or nanoparticles of silver, copper, or nickel, and nano-inks and paste inks of silver or copper.

The metal precursor ink may be deposited by a suitable coating or printing technique to form a thin film. The coating or printing technique is selected from spin coating, pipetting, blade coating, bar coating, rod coating, roll coating, spray coating, curtain coating, dip coating, flow coating, comma coating, slot die coating, dispensing, casting, stamping, imprinting, pad printing, inkjet printing, offset printing, screen printing, gravure printing, flexography printing, and lithography.

The coated thin film or patterned film may be chemically treated with a liquid or vapor phase acid, a basic compound or a chemical, such as an oxidizing agent or a reducing agent. Alternatively, the coated thin film or patterned film may be physically treated, for example, heat, plasma, IR, UV, electron beam, laser, microwave, electrically or magnetically treated. A combination of the chemical and physical treatments may be applied to the coated thin film or patterned film. This post-treatment makes the film highly conductive in a more rapid manner.

The post-treatment process may be carried out under heating in a general inert atmosphere. If needed, the post-treatment process may be carried out in air, nitrogen, carbon monoxide, a hydrogen/air mixture or a mixed gas thereof. The post-treatment is typically performed at 400° C. or less, preferably 250° C. or less. The post-treatment temperature may be increased or decreased depending on the kind of a substrate used. The post-treatment time is not particularly limited but is preferably as short as possible so long as serious problems are not caused in a batch or continuous process.

The present invention will be explained with reference to the following examples. However, these examples are merely illustrative and the scope of the present invention is not limited thereto.

EXAMPLES

Synthesis of compounds for metal precursors

Synthesis Example 1

Synthesis of dimethyl 2-(hydroxyimino)malonate

A solution of 76 mL of glacial acetic acid and 10 g of sodium hydroxide in 30 mL of water was slowly added to a 500 mL three-neck flask equipped with a stirrer, and then a solution of 10 g of dimethyl malonate in 20 mL of glacial acetic acid was added thereto. The mixture was cooled in an ice bath. To the mixture was slowly added dropwise a solution of 52.2 g of sodium nitrite ($NaNO_2$) in 76 mL of water through a dropping funnel while maintaining the temperature at 5° C. or less. After completion of the dropwise addition, the temperature was slowly raised to room temperature. The resulting mixture was allowed to react for 24 h with stirring. After the reaction was finished, the reaction mixture was diluted with 500 mL of water and extracted thrice with 500 mL of ethyl acetate. The organic layer was carefully washed with an aqueous solution of sodium bicarbonate ($NaHCO_3$) until the water layer became alkaline. The resulting organic layer was dried over anhydrous sodium sulfate, filtered, and evaporated to remove the solvent using a vacuum pump. The residual viscous liquid was purified by column chromatography, affording the title product (58.5 g, yield 95%, m.p. 64-65° C.) as a white solid, $^1$H NMR ($CDCl_3$); d 3.897 (s, —$CH_3$), 3.929 (s, —$CH_3$), 10.864 (br, —OH)

Synthesis Example 2

Synthesis of dimethyl 2-(methoxyimino)malonate 16.1 g (0.1 mol) of dimethyl 2-(hydroxyimino)malonate and 85.1 g (0.6 mol) of methyl iodide were placed in a 250 mL three-neck flask equipped with a stirrer, and 27.8 g (0.12 mol) of silver oxide ($Ag_2O$) was slowly added portionwise thereto. After stirring at room temperature for 30 min, the reaction temperature was slowly raised to 50° C. The mixture was continued for additional 12 h. After completion of the reaction, the reaction mixture was added with 150 mL of ethyl ether, filtered, and evaporated to remove the solvent, affording 16.8 g (yield 96%) of the title product as a colorless, transparent liquid. $^1$H NMR ($CDCl_3$); d 3.850 (s, 3H, —$CH_3$), 3.854 (s, 3H, —$CH_3$), 4.073 (s, 3H, —$OCH_3$)

Synthesis Example 3

Synthesis of dimethyl 2-(allyloxyimino)malonate 16.1 g (0.1 mol) of dimethyl 2-(hydroxyimino)malonate and 13.3 g (0.11 mol) of allyl bromide were placed in a 250 mL flask equipped with a stirrer, and 15.2 g (0.11 mol) of potassium carbonate and 150 mL of acetone as a solvent were added thereto. The mixture was allowed to react at 90° C. for 24 h. After completion of the reaction, the solvent was vaporized in vacuo. The remaining reaction mixture was added to 250 mL of water and extracted with ethyl acetate. The organic layer was dried over anhydrous sodium sulfate, filtered, and evaporated to remove the solvent. The residual red liquid was purified by column chromatography (hexane:ethyl acetate=7:3), affording 14.8 g (yield 73.6%) of the title product as a pale yellow liquid. $^1$H NMR ($CDCl_3$); d 3.891 (s, 3H, —$CH_3$), 3.903 (s, 3H, —$CH_3$), 4.800-4.821 (m, 2H, —$CH_2$), 5.266-5.365 (m, 2H, =$CH_2$), 5.920-6.018 (m, 1H, —CH)

Synthesis Example 4

Synthesis of dimethyl 2-(propargyloxyimino)malonate 16.1 g (0.1 mol) of dimethyl 2-(hydroxyimino)malonate and 16.4 g (80% toluene solution, 0.11 mol) of propargyl bromide were placed in a 250 mL flask equipped with a stirrer, and 15.2 g (0.11 mol) of potassium carbonate and 150 mL of acetone as a solvent were added thereto. The mixture was allowed to react at 90° C. for 24 h. After completion of the reaction, the solvent was vaporized in vacuo. The remaining reaction mixture was added to 250 mL of water and extracted with ethyl acetate. The organic layer was dried over anhydrous sodium sulfate, filtered, and evaporated to remove the solvent. The residual red liquid was purified by column chromatography (hexane:ethyl acetate=7:3), affording 15.1 g (yield 75.9%) of the title product as a pale yellow liquid. $^1$H NMR ($CDCl_3$); d 2.575 (t, 1H, CH), 3.904 (s, 3H, —$CH_3$), 3.915 (s, 3H, —$CH_3$), 4.878, 4.884 (d, 2H, —$CH_2$)

Synthesis Example 5

Synthesis of dimethyl 2-(2-ethylhexyloxyimino)malonate 16.1 g (0.1 mol) of dimethyl 2-(hydroxyimino)malonate and 19.3 g (0.1 mol) of 2-ethylhexyl bromide were placed in a 500 mL three-neck flask equipped with a stirrer, and 15.2 g (0.11 mol) of potassium carbonate and 150 mL of DMF as a solvent were added thereto. The mixture was allowed to react at 90° C. for 24 h. After completion of the reaction, the reaction mixture was added to 500 mL of water, extracted with chloroform, dried over anhydrous sodium sulfate, and evaporated to remove the solvent. The residual red liquid was purified by column chromatography (hexane:ethyl acetate=9:1), affording 20.7 g (yield 75%) of the title product as a pale yellow liquid. $^1$H NMR (CDCl$_3$); d 0.823-0.875 (m, 6H, —CH$_3$), 1.237-1.347 (m, 10H, —CH$_2$), 1.607-1.683 (m, 1H, —CH), 3.844 (s, 3H, —CH$_3$), 3.8479 (s, 3H, —CH$_3$)

Preparation of Metal Precursors

Example 1

Preparation of silver 2-(hydroxyimino)malonate 16.1 g (0.1 mol) of dimethyl 2-(hydroxyimino)malonate was added to 200 mL of a 1.0 N aqueous NaOH solution. The mixture was allowed to react at room temperature for 24 h with stirring. After completion of the reaction, the reaction mixture was adjusted to a pH of 7.0 with a dilute aqueous solution of nitric acid and an aqueous solution of 34.0 g (0.2 mol) of silver nitrate in 200 mL of water was slowly added dropwise thereto to precipitate a white solid. The precipitate was filtered, sufficiently washed sequentially with water and methanol, and dried in a vacuum oven, affording 33.5 g (yield 96.5%) of the title product as a white solid.

Example 2

Preparation of silver 2-(hydroxyimino)malonate 18.9 g (0.1 mol) of diethyl 2-(hydroxyimino)malonate was added to 250 mL of a 10% ethanolic KOH solution. The mixture was allowed to react under reflux for 12 h. After completion of the reaction, the reaction mixture in the form of slurry was dissolved in 250 mL of distilled water to obtain a transparent solution. A dilute aqueous solution of nitric acid was added to the solution until the pH reached 7.0 and an aqueous solution of 34.0 g (0.2 mol) of silver nitrate in 100 mL of water was slowly added dropwise to precipitate a white solid. The precipitate was filtered, sufficiently washed sequentially with water and methanol, and dried in a vacuum oven, affording 33.2 g (yield 95.7%) of the title product as a white solid.

Example 3

Preparation of silver 2-(2-ethylhexyloxyimino)malonate 5.5 g (0.02 mol) of dimethyl 2-(2-ethylhexyloxyimino)malonate was added to 40 mL of a 1.0 N aqueous solution of NaOH. The mixture was allowed to react at room temperature for 24 h with stirring and at 40° C. for additional 3 h. After completion of the reaction, the reaction mixture was adjusted to a pH of 7.0 with a dilute aqueous solution of nitric acid and an aqueous solution of 6.8 g (0.04 mol) of silver nitrate in 50 mL of water was slowly added dropwise thereto to precipitate a solid. The precipitate was filtered, sufficiently washed sequentially with water and methanol, and dried in a vacuum oven, affording 8.9 g (yield 97%) of the title product as a white solid. NMR (DMSO-d6); 0.824-0.861 (m, br, 6H, —CH$_3$), 1.238 (m, br 10H, —CH$_2$), 1.756 (m, br, 1H, —CH)

Example 4

Preparation of silver 2-(methoxyimino)malonate 8.7 g (0.05 mol) of dimethyl 2-(methoxyimino)malonate was added to 100 mL of a 1.0 N aqueous solution of NaOH. The mixture was allowed to react at room temperature for 24 h with stirring. After completion of the reaction, the reaction mixture was adjusted to a pH of 7.0 with a dilute aqueous solution of nitric acid and an aqueous solution of 17.0 g (0.1 mol) of silver nitrate in 100 mL of water was slowly added dropwise thereto to precipitate a solid. The precipitate was filtered, sufficiently washed sequentially with water and methanol, and dried in a vacuum oven, affording 17.1 g (yield 95%) of the title product as a solid.

Example 5

Preparation of silver 2-(allyloxyimino)malonate 4.02 g (0.02 mol) of dimethyl 2-(allyloxyimino)malonate was added to 40 mL of a 1.0 N aqueous solution of NaOH. The mixture was allowed to react at room temperature for 24 h with stirring and at 40° C. for additional 3 h. After completion of the reaction, the reaction mixture was adjusted to a pH of 7.0 with a dilute aqueous solution of nitric acid and an aqueous solution of 6.80 g (0.04 mol) of silver nitrate in 50 mL of water was slowly added dropwise thereto to precipitate a solid. The precipitate was filtered, sufficiently washed sequentially with water and methanol, and dried in a vacuum oven, affording 8.15 g (yield 98%) of the title product as a solid.

Example 6

Preparation of silver 2-(propargyloxyimino)malonate 3.98 g (0.02 mol) of dimethyl 2-(propargyloxyimino) malonate was added to 40 mL of a 1.0 N aqueous solution of NaOH. The mixture was allowed to react at room temperature for 24 h with stirring and at 40° C. for additional 3 h. After completion of the reaction, the reaction mixture was adjusted to a pH of 7.0 with a dilute aqueous solution of nitric acid and an aqueous solution of 6.80 g (0.04 mol) of silver nitrate in 50 mL of water was slowly added dropwise thereto to precipitate a solid. The precipitate was filtered, sufficiently washed sequentially with water and methanol, and dried in a vacuum oven, affording 8.10 g (yield 98%) of the title product as a solid.

Example 7

Preparation of copper (II) 2-(hydroxyimino)malonate 1.61 g (0.01 mol) of dimethyl 2-(hydroxyimino)malonate was added to 20 mL of a 1.0 N aqueous solution of NaOH. The mixture was allowed to react at room temperature for 24 h with stirring. After completion of the reaction, the reaction mixture was adjusted to a pH of 7.0 with a dilute aqueous solution of nitric acid and an aqueous solution of 2.42 g (0.02 mol) of copper nitrate (Cu(NO$_3$)$_2$.3H$_2$O) in 20 mL of water was slowly added dropwise thereto to precipitate a solid. The precipitate was filtered, sufficiently washed sequentially with water and methanol, and dried in a vacuum oven, affording 2.3 g of the title product as a deep green solid.

Example 8

Preparation of copper (II) 2-(2-ethylhexyloxyimino)malonate 1.37 g (5.0 mmol) of dimethyl 2-(2-ethylhexyloxyimino)malonate was added to 10 mL of a 1.0 N aqueous solution of NaOH. The mixture was allowed to react at room temperature for 24 h with stirring and at 40° C. for additional 3 h. After completion of the reaction, the reaction mixture was adjusted to a pH of 7.0 with a dilute aqueous solution of nitric acid and an aqueous solution of 1.33 g (5.5 mmol) of copper nitrate ($Cu(NO_3)_2 \cdot 3H_2O$) in 10 mL of water was slowly added dropwise thereto to precipitate a solid. The precipitate was filtered, sufficiently washed sequentially with water and methanol, and dried in a vacuum oven, affording 1.3 g of the title product as a pale green solid.

Example 9

Preparation of cobalt (II) 2-(hydroxyimino)malonate 1.61 g (0.01 mol) of dimethyl 2-(hydroxyimino)malonate was added to 20 mL of a 1.0 N aqueous solution of NaOH. The mixture was allowed to react at room temperature for 24 h with stirring. After completion of the reaction, the reaction mixture was adjusted to a pH of 7.0 with a dilute aqueous solution of nitric acid and an aqueous solution of 2.91 g (0.02 mol) of cobalt nitrate ($Co(NO_3)_2 \cdot 6H_2O$) in 20 mL of water was slowly added dropwise thereto to precipitate a solid. The precipitate was filtered, sufficiently washed sequentially with water and methanol, and dried in a vacuum oven, affording 1.5 g of the title product as a red solid.

Example 10

Preparation of silver 2-(hydroxyimino)glyoxylate 5.16 g (0.058 mol) of 2-(hydroxyimino)glyoxylic acid was dissolved in 50 mL of methanol and an aqueous solution of 2.32 g (0.058 mol) of sodium hydroxide (NaOH) in 50 mL of water was slowly added thereto. The mixture was allowed to react at room temperature for 3 h with stirring. The reaction mixture was adjusted to a pH of 7.0 with a dilute aqueous solution of nitric acid and an aqueous solution of 9.86 g (0.058 mol) of silver nitrate ($AgNO_3$) in 50 mL of water was slowly added dropwise thereto to precipitate a white solid. The precipitate was filtered, sufficiently washed sequentially with water and methanol, and dried in a vacuum oven, affording 10.9 g (yield 96%) of the title product as a white solid.

Example 11

Preparation of silver 2-(hydroxyimino)pyruvate 5.97 g (0.058 mol) of 2-(hydroxyimino)pyruvic acid was dissolved in 50 mL of methanol and a solution of 2.32 g (0.058 mol) of sodium hydroxide (NaOH) in 50 mL of water was slowly added thereto. The mixture was allowed to react at room temperature for 3 h with stirring. The reaction mixture was adjusted to a pH of 7.0 with a dilute aqueous solution of nitric acid and an aqueous solution of 9.86 g (0.058 mol) of silver nitrate ($AgNO_3$) in 50 mL of water was slowly added dropwise thereto to precipitate a white solid. The precipitate was filtered, sufficiently washed sequentially with water and methanol, and dried in a vacuum oven, affording 11.2 g (yield 92%) of the title product as a white solid.

Example 12

Preparation of silver 2-(methoxyimino)pyruvate 6.79 g (0.058 mol) of 2-(methoxyimino)pyruvic acid was dissolved in 50 mL of methanol and an aqueous solution of 2.32 g (0.058 mol) of sodium hydroxide (NaOH) in 50 mL of water was slowly added thereto. The mixture was allowed to react at room temperature for 3 h with stirring. The reaction mixture was adjusted to a pH of 7.0 with a dilute aqueous solution of nitric acid and an aqueous solution of 9.86 g (0.058 mol) of silver nitrate ($AgNO_3$) in 50 mL of water was slowly added dropwise thereto to precipitate a white solid. The precipitate was filtered, sufficiently washed sequentially with water and methanol, and dried in a vacuum oven, affording 11.4 g (yield 88%) of the title product as a white solid.

Example 13

Preparation of Silver Nitrilotriacetate 14.91 g (0.058 mol) of nitrilotriacetic acid trisodium salt was dissolved in 100 mL of distilled water and a solution of 29.58 g (0.174 mol) of silver nitrate ($AgNO_3$) in 50 mL of distilled water was slowly added dropwise with stirring thereto to precipitate a white solid. The precipitate was filtered, sufficiently washed sequentially with water and methanol, and dried in a vacuum oven, affording 28.2 g of (yield 95%) of the title product as a solid.

Example 14

Preparation of copper (II) 2-(hydroxyimino)glyoxylate 0.89 g (10 mmol) of 2-(hydroxyimino)glyoxylic acid was added to 10 mL of a 1.0 N aqueous NaOH solution. The mixture was allowed to react at room temperature for 24 h with stirring. After completion of the reaction, the reaction mixture was adjusted to a pH of 7.0 with a dilute aqueous solution of nitric acid and an aqueous solution of 1.33 g (5.5 mmol) of copper nitrate ($Cu(NO_3)_2 \cdot 3H_2O$) in 10 mL of water was slowly added dropwise thereto to precipitate a solid. The precipitate was filtered, sufficiently washed sequentially with water and methanol, and dried in a vacuum oven, affording 1.1 g of the title product as a bluish green solid.

Example 15

Preparation of silver 2-(hydroxyimino)malonate-di[tris(tributylphosphine)] complex 2.08 g (6 mmol) of the silver precursor compound (silver 2-(hydroxyimino)malonate) prepared in Example 1 was added to 50 mL of anhydrous tetrahydrofuran (THF) under a nitrogen atmosphere. The mixture was sufficiently stirred to obtain slurry. To the slurry was added 7.28 g (36 mmol) of tributylphosphine. The resulting mixture was allowed to react at room temperature for 24 h. A slight amount of unreacted reactants were filtered off and the filtrate was evaporated to remove volatiles using a vacuum pump, affording 8.5 g (90.8%) of the title product as a viscous liquid.

Production of Metal Precursor Inks

Example 16

2.0 g of aqueous ammonia (ammonia content 28-30 wt %) was slowly added dropwise to 2.0 g of the silver precursor compound (silver 2-(hydroxyimino)malonate) prepared in Example 1. To the resulting clear solution were sequentially added 0.8 g of 50 wt % aqueous ammonium formate, 1.0 g of 2,3-butanediol, 1.0 g of methanol, and 0.4 g of 2-amino-2-methyl-1-propanol. After sufficient mixing, the mixture was passed through a 0.45 micron Teflon filter to obtain a transparent silver precursor ink. The ink was found to have a viscosity of 6.8 cps and a surface tension of 28.5 dyne/cm. The composition was stable at room temperature in air and was inkjet printable. The composition was spin coated on a PET film and sintered at 140° C. for 10 min. As a result, a silver film was well formed. The film was measured to have a conductivity (resistivity) of 1.5 Ω/□.

Example 17

7.0 g of an aqueous solution of ammonium carbamate (30 wt %) was slowly added dropwise to 3.0 g of the silver precursor compound (silver 2-(hydroxyimino)malonate) prepared in Example 2. The mixture was sufficiently stirred to obtain a clear solution. To the solution were sequentially added 1.0 g of 50 wt % aqueous ammonium formate, 1.5 g of 2,3-butanediol, 1.5 g of methanol, and 0.5 g of 2-amino-2-methyl-1-propanol. After sufficient mixing, the mixture was passed through a 0.45 micron Teflon filter to obtain a transparent silver precursor ink. The ink was spin coated on a PET film and sintered at 150° C. for 10 min. As a result, a silver film was well formed. The film was measured to have a conductivity (resistivity) of 2.5 Ω/□.

Example 18

A solution of 2.0 g of the silver precursor compound (silver 2-(hydroxyimino)malonate) prepared in Example 2 in 2.0 g of aqueous ammonia (ammonia content 28-30 wt %) was sufficiently mixed with a solution of 1.0 g of silver oxide in 3.0 g of an aqueous solution of ammonium carbamate (30 wt %). To the complex solution were sequentially added 1.0 g of 50 wt % aqueous ammonium formate, 1.0 g of 2,3-butanediol, 2.0 g of methanol, and 0.6 g of 2-amino-2-methyl-1-propanol. After sufficient mixing, the mixture was passed through a 0.45 micron Teflon filter to obtain a transparent silver complex precursor ink. The ink was spin coated on a PET film and c sintered at 140° C. for 10 min. As a result, a silver film was well formed. The film was measured to have a conductivity (resistivity) of 1.9 Ω/□.

Example 19

2.0 g of the silver precursor compound (silver 2-(hydroxyimino)malonate) prepared in Example 1 and 1.0 g of silver oxide were slowly added dropwise to 3.0 g of aqueous ammonia (ammonia content 28-30 wt %). The mixture was sufficiently stirred and 1.0 g of an aqueous solution of ammonium carbamate (30 wt %) was slowly added dropwise thereto. After sufficient stirring, to the complex solution were sequentially added 1.0 g of 50 wt % aqueous ammonium formate, 0.5 g of diethanolamine, 0.5 g of 2,3-butanediol, 2.0 g of methanol, and 0.6 g of 2-amino-2-methyl-1-propanol. After sufficient mixing, the mixture was passed through a 0.45 micron Teflon filter to obtain a transparent silver complex precursor ink. The ink was spin coated on a PET film and sintered at 150° C. for 10 min. As a result, a silver film was well formed. The film was measured to have a conductivity (resistivity) of 1.7 Ω/□.

Example 20

3.5 g of isobutylamine was sufficiently mixed with 2.0 g of the silver precursor compound (silver 2-(2-ethylhexyloxyimino)malonate) prepared in Example 3 to obtain a solution. To the solution were sequentially added 0.5 g of aqueous ammonia (ammonia content 28-30 wt %), 0.8 g of 50 wt % aqueous ammonium formate, 1.5 g of methanol, and 0.4 g of 2-amino-2-methyl-1-propanol. The mixture was sufficiently stirred to obtain a silver ink. The ink was found to have a viscosity of 8.8 cps and a surface tension of 27.3 dyne/cm. The composition was stable at room temperature in air and was inkjet printable. The mixed solution was passed through a 0.45 micron Teflon filter to obtain a transparent silver precursor ink. The ink was spin coated on a PET film and sintered at 150° C. for 10 min. As a result, a specular silver film was formed. The film was measured to have a conductivity (resistivity) of 9.7 Ω/□.

Example 21

3.0 g of isobutylamine was added to 1.0 g of the copper 2-(2-ethylhexyloxyimino)malonate prepared in Example 8. The mixture was dissolved with sufficient stirring. To the solution were sequentially added 0.5 g of aqueous ammonia (ammonia content 28-30 wt %), 0.8 g of 50 wt % aqueous ammonium formate, 1.5 g of methanol, and 0.4 g of 2-amino-2-methyl-1-propanol. After sufficient mixing, the mixed solution was filtered through a 0.45 micron Teflon filter to obtain a transparent blue copper precursor ink.

Example 22

1.5 g of aqueous ammonia (ammonia content 28-30 wt %) was slowly added dropwise to 2.0 g of the silver 2-(hydroxyimino)glyoxylate prepared in Example 10 to obtain a clear solution. To the solution were sequentially added 0.8 g of 50 wt % aqueous ammonium formate, 1.0 g of 2,3-butanediol, 1.0 g of methanol, and 0.4 g of 2-amino-2-methyl-1-propanol. After sufficient mixing, the mixed solution was filtered through a 0.45 micron Teflon filter to obtain a transparent silver precursor ink. The ink was spin coated on a PET film and sintered at 140° C. for 10 min. As a result, a silver film was formed. The film was measured to have a conductivity (resistivity) of 3.5 Ω/□.

Example 23

3.2 g of isobutylamine was added to 2.0 g of the silver precursor compound (silver 2-(hydroxyimino)pyruvate) prepared in Example 11. The mixture was dissolved with sufficient stirring. To the solution were sequentially added 0.5 g of aqueous ammonia (ammonia content 28-30 wt %), 0.6 g of 50 wt % aqueous ammonium formate, 1.2 g of methanol, and 0.4 g of 2-amino-2-methyl-1-propanol. The mixture was sufficiently stirred to obtain a silver ink. The ink was found to have a viscosity of 6.4 cps and a surface tension of 27.5 dyne/cm. The composition was stable at room temperature in air and was inkjet printable. The mixed solution was passed through a 0.45 micron Teflon filter to obtain a transparent silver precursor ink. The silver ink composition was spin coated on a PET film and the thin film was sintered at 140° C. for 10 min. As a result, a specular silver film was formed. The film was measured to have a conductivity (resistivity) of 5.0 Ω/□.

Example 24

2.0 g of the silver precursor compound (silver 2-(hydroxyimino)malonate) prepared in Example 1 was dissolved in 2.g of aqueous ammonia (ammonia content 28-30 wt %). To the solution were sequentially added 1.0 g of the silver precursor compound (silver 2-(hydroxyimino)pyruvate) prepared in Example 11, 2.0 g of isobutylamine, 0.6 g of 50 wt % aqueous ammonium formate, 0.3 g of propylene glycol, 0.3 g of methanol, and 0.3 g of 2-amino-2-methyl-1-propanol. After sufficient stirring, the mixed solution was passed through a 0.45 micron Teflon filter to obtain a transparent silver precursor ink. The ink was spin coated on a PET film and sintered at 150° C. for 20 min. As a result, a silver film was well formed. The film was measured to have a conductivity (resistivity) of 0.7 Ω/□.

Example 25

3.5 g of isobutylamine was added to 2.0 g of the silver precursor compound (silver 2-(methoxyimino)pyruvate) prepared in Example 12. The mixture was dissolved with sufficient stirring. To the solution were sequentially added 0.4 g of aqueous ammonia (ammonia content 28-30 wt %), 0.6 g of 50 wt % aqueous ammonium formate, 1.5 g of ethanol, and 0.4 g of 2-amino-2-methyl-1-propanol. After sufficient stirring, the mixed solution was passed through a 0.45 micron Teflon filter to obtain a transparent silver precursor ink. The ink was found to have a viscosity of 6.5 cps and a surface tension of 27.6 dyne/cm. The composition was stable at room temperature in air and was inkjet printable. The mixed solution was passed through a 0.45 micron Teflon filter to obtain a transparent silver precursor ink. The silver ink composition was spin coated on a PET film and sintered at 140° C. for 10 min. As a result, a specular silver film was formed. The film was measured to have a conductivity (resistivity) of 5.4 Ω/□.

Example 26

1.0 g of the silver precursor compound (silver nitrilotriacetate) prepared in Example 11 and 1.0 g of the silver precursor compound (silver 2-(2-ethylhexyloxyimino)malonate) prepared in Example 3 were sufficiently mixed with 4.0 g of isobutylamine and 0.5 g of ethylhexylamine. To the mixture were sequentially added 0.6 g of 50 wt % aqueous ammonium formate, 1.0 g of methanol, and 0.4 g of 2-amino-2-methyl-1-propanol. After sufficient stirring, the mixed solution was passed through a 0.45 micron Teflon filter to obtain a transparent silver precursor ink. The ink was spin coated on a PET film and sintered at 150° C. for 20 min. As a result, a silver film was well formed. The film was measured to have a conductivity (resistivity) of 3.5 Ω/□.

Measurements and Evaluations

1) Conductivity was evaluated by measuring the sheet resistance of a patterned rectangular sample (1 cm×3 cm) with a four-point probe (CMT-SR1000N, AIT).

2) Ink Stability was evaluated by observing whether silver was reduced after standing of each ink at room temperature for 48 h.

3) Inkjet printing was performed by ejecting each ink at room temperature with a Dimatix DMP-2831 (10 pl nozzle) inkjet printer.

4) Viscosity was measured using a Brookfield DV-II+ PRO LV (spindle: CPE-40) viscometer.

5) Surface tension was measured using a tension meter (Surface Tensiomat 21).

The invention claimed is:

1. A metal precursor represented by the following General Formula 1:

[General Formula 1]

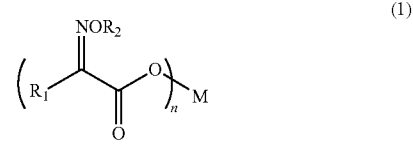

wherein $R_1$ and $R_2$ are each independently hydrogen, halogen, amino, nitro, cyano, hydroxyl, substituted or unsubstituted C1-C30 alkyl, substituted or unsubstituted C3-C30 cycloalkyl, substituted or unsubstituted C6-C30 aryl, substituted or unsubstituted C6-C30 aralkyl, substituted or unsubstituted C1-C30 heteroalkyl, substituted or unsubstituted C2-C30 heterocycloalkyl, substituted or unsubstituted C5-C30 heteroaryl, substituted or unsubstituted C5-C30 heteroaralkyl, —$(CH_2)_jORa$, —$(CH_2)_jC(O)Ra$, —$(CH_2)_jC(O)ORa$, —$(CH_2)_jOC(O)Ra$, —$(CH_2)_jOM$, —$(CH_2)_jC(O)M$, —$(CH_2)_jC(O)OM$, —$(CH_2)_jOC(O)M$, —$(CH_2)_jNRbRc$, $(CH_2)_jC(O)NRbRc$, —$(CH_2)_jOC(O)NRbRc$, —$(CH_2)_jNRdC(O)Rb$, —$(CH_2)_jNRdC(O)ORb$, $(CH_2)_jNRdC(O)NRbRc$, —$(CH_2)_jS(O)mRe$ or —$(CH_2)_jNRdS(O)mM$, where j is an integer from 0 to 12, m is an integer from 0 to 2, and Ra, Rb, Rc, Rd, and Re are each independently hydrogen, halogen, amino, nitro, cyano, hydroxyl, substituted or unsubstituted C1-C30 alkyl, substituted or unsubstituted C3-C30 cycloalkyl, substituted or unsubstituted C6-C30 aryl, substituted or unsubstituted C6-C30 aralkyl, substituted or unsubstituted C1-C30 heteroalkyl, substituted or unsubstituted C2-C30 heterocycloalkyl, substituted or unsubstituted C5-C30 heteroaryl, or substituted or unsubstituted C5-C30 heteroaralkyl, n is an integer from 1 to 4, and M is selected from the group consisting of Ag, Ni, Co, Mn, Au, Pt, Pd, Sb, Bi, Pb, and Ti.

2. The metal precursor according to claim 1, wherein the metal precursor of the above General Formula 1 is a compound selected from the group consisting of compounds represented by the following General Formulae 2 to 5:

[General Formula 2]

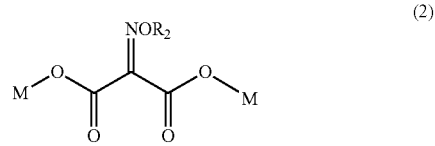

[General Formula 3]

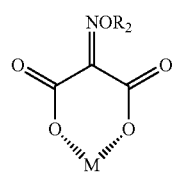
(3)

[General Formula 4]

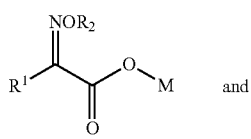 and
(4)

[General Formula 5]

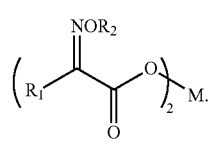
(5)

3. The metal precursor according to claim 1, wherein the metal precursor of the following General Formula 1 is a compound selected from the group consisting of compounds represented by following Formulae 1 to 15:

[Formula 1]

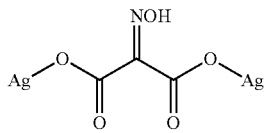
(I)

[Formula 2]

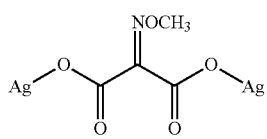
(II)

[Formula 3]

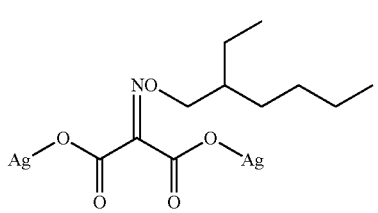
(III)

[Formula 4]

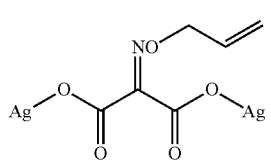
(IV)

[Formula 5]

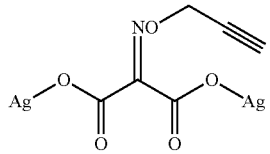
(V)

[Formula 6]

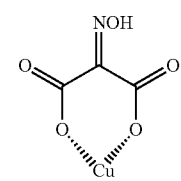
(VI)

[Formula 7]

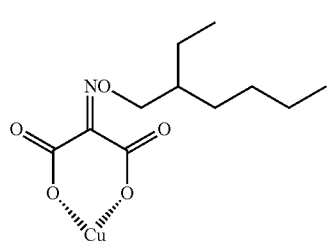
(VII)

[Formula 8]

(VIII)

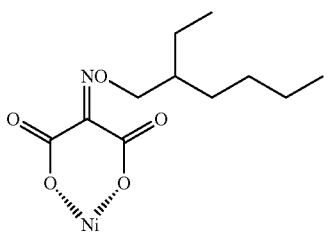

[Formula 9]

(IX)

[Formula 10]

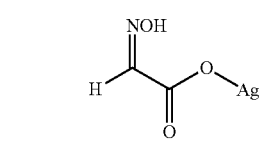
(X)

[Formula 11]

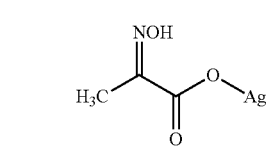
(XI)

[Formula 12]

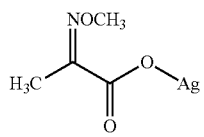

(XII)

[Formula 13]

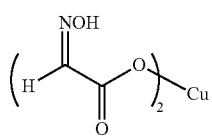

(XIII)

[Formula 14]

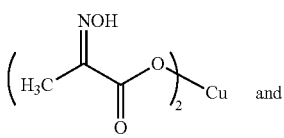 and (XIV)

[Formula 15]

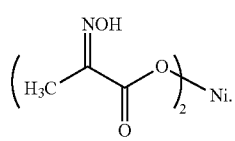

(XV)

4. The metal precursor according to claim 1, wherein $R_1$ and $R_2$ are each independently selected from the group consisting of hydrogen, methyl, ethyl, n-propyl, iso-propyl, n-butyl, iso-butyl, t-butyl, n-pentyl, amyl, n-hexyl, 2-ethylhexyl, n-heptyl, octyl, iso-octyl, nonyl, decyl, dodecyl, hexadecyl, octadecyl, docodecyl, cyclopropyl, cyclopentyl, cyclohexyl, allyl, propargyl, acetyl, benzoyl, hydroxyethyl, methoxyethyl, 2-hydroxypropyl, methoxypropyl, aminoethyl, cyanoethyl, mercaptoethyl, chloroethyl, methoxy, ethoxy, butoxy, hexyloxy, phenoxy, methoxyethoxyethyl, methoxyethoxy ethoxy ethyl, imidazole, carboxymethyl, trimethoxysilylpropyl, triethoxysilylpropyl, phenyl, methoxyphenyl, cyanophenyl, tolyl, benzyl, and carboxylic acid metal salts.

5. A metal precursor ink comprising one or more kinds of the metal precursor according to claim 1; and one or more additives selected from the group consisting of a solvent, a complexing agent, a resin, a stabilizer, a dispersant, a reducing agent, a coupling agent, a leveling agent, a surfactant, a wetting agent, a thickening agent, and a thixotropic agent.

6. The metal precursor ink according to claim 5, wherein the complexing agent is a sigma-electron donor or a phi-electron donor.

7. The metal precursor ink according to claim 6, wherein the electron donor is used in an amount of 0.5 to 95% by weight, based on the weight of the metal precursor.

8. The metal precursor ink according to claim 5, wherein the additives are one or more selected from the group consisting of ammonia, ammonium formate, ammonium carbamate, diethanolamine, 2,3-butanediol, methanol, and 2-amino-2-methyl-1-propanol.

9. The metal precursor ink according to claim 5, wherein the viscosity of the ink for inkjet printing is in the range of 0.1 to 50 cps, as measured at room temperature 20° C.

10. The metal precursor ink according to claim 5, wherein the metal precursor has double bond or triple bond in the molecule to induce phi bond complexation.

11. A hybrid ink produced by mixing or reacting the metal precursor ink according to claim 5, with one or more materials one or more selected from the group consisting of other metal precursor compounds, metal powders, metal nanoparticles, and inks produced therefrom.

12. A conductive thin film formed by deposition of the metal precursor ink according to claim 5.

13. A conductive thin film formed by deposition of the metal precursor ink according to claim 6.

14. A conductive thin film formed by deposition of the metal precursor ink according to claim 7.

15. A conductive thin film formed by deposition of the metal precursor ink according to claim 8.

16. A conductive thin film formed by deposition of the metal precursor ink according to claim 9.

17. A conductive thin film formed by deposition of the metal precursor ink according to claim 10.

18. A conductive thin film formed by deposition of the metal precursor ink according to claim 11.

* * * * *